United States Patent [19]

Richards

[11] Patent Number: 5,645,987
[45] Date of Patent: Jul. 8, 1997

[54] ENZYMATIC SYNTHESIS OF OLIGONUCLEOTIDES

[75] Inventor: Rodney M. Richards, Louisville, Colo.

[73] Assignee: Amgen Inc., Thousand Oaks, Calif.

[21] Appl. No.: 200,897

[22] Filed: Feb. 23, 1994

Related U.S. Application Data

[63] Continuation of Ser. No. 50,712, Apr. 19, 1993, abandoned, which is a continuation of Ser. No. 762,140, Sep. 23, 1991, abandoned, which is a continuation of Ser. No. 586,368, Sep. 21, 1990, abandoned.

[51] Int. Cl.$^6$ .................... C12P 19/34; C12Q 1/68
[52] U.S. Cl. .................... 435/6; 435/91.2; 935/77; 935/78
[58] Field of Search .................... 435/91.1, 6, 91.2; 935/77, 78

[56] References Cited

U.S. PATENT DOCUMENTS 4,994,368  2/1991  Goodman et al. .................... 436/94

FOREIGN PATENT DOCUMENTS

| 89/09284 | 10/1989 | WIPO . |
| 92/01813 | 2/1992 | WIPO . |
| 92/05287 | 4/1992 | WIPO . |

*Primary Examiner*—Stephanie W. Zitomer
*Attorney, Agent, or Firm*—Joan D. Eggert; Steven M. Odre; Ron K. Levy

[57] ABSTRACT

The present invention makes possible the catalytic production of sequence specific oligonucleotides through the use of a specially designed template sequence. The reaction can be made to proceed isothermally in the presence of an excess of nucleoside triphosphates, an agent for polymerization, and a cutting agent. Because the process is catalytic with respect to the template sequence, an unlimited amount of oligonucleotide product can theoretically be generated from a single molecule of template. Where the process is initiated by the presence of a nucleic acid target sequence, the method of the present invention can be used for diagnostic purposes as an amplification method to improve sensitivity. Diagnostic sensitivity can be further enhanced by employing a cascade of these template sequences.

44 Claims, 25 Drawing Sheets

RS = Restriction Endonuclease Recognition Sequence

X = Cutting Attenuation Modification

CP = Cleavage Product

RS = Restriction Endonuclease Recognition Sequence

X = Cutting Attenuation Modification

CP = Cleavage Product

RS = Restriction Endonuclease Recognition Sequence

X = Cutting Attenuation Modification

SP1, SP2 = Substrate Precursors

RS = Restriction Endonuclease Recognition Sequence

X = Cutting Attenuation Modification

CS = Restriction Endonuclease Cleavage Site

RS = Restriction Endonuclease Recognition Sequence

X = Cutting Attenuation Modification

A = Region to be Amplified

P = Catalytic Primer
CS = Restriction Endonuclease Cleavage Site
RS = Restriction Endonuclease Recognition Sequence
X = Cutting Attenuation Modification X = Cutting Attenuation Modification RS = Restriction Endonuclease Recognition Sequence X = Cutting Attenuation Modification RS = Restriction Endonuclease Recognition Sequence X = Cutting Attenuation Modification
RRS = Remote Recognition Sequence
RCS = Remote Cutting Site I. Phosphate II. Methylphosphonate III. Methylthiophosphonate

* = Radioactive Adenosine Residues

* = Radioactive Adenosine Residues

ENZYMATIC SYNTHESIS OF OLIGONUCLEOTIDES

This application is a continuation of application Ser. No. 08/050,712, filed Apr. 19, 1993, now abandoned, which is a continuation of Ser. No. 07/762,140 filed Sep. 23, 1991, now abandoned, which is a continuation of Ser. No. 07/586,368 filed Sep. 21, 1990 and now abandoned.

BACKGROUND

Sequence specific oligonucleotides are used extensively in the fields of molecular biology and probe diagnostics for such varied purposes as, for example, site directed mutagenesis, gene assembly, and as DNA probes to identify the presence of specific nucleic acid sequences in patient test samples. In addition, oligonucleotide probe mixtures have been prepared in research laboratories, based on the protein sequence of a resulting gene product and the degeneracy of the DNA code, to identify and characterize the nucleic acid sequences responsible for encoding these gene products. Even more recently, research has been directed toward the use of oligonucleotide sequences in a field which has become known as "antisense" therapy, whereby the oligonucleotides act as therapeutic agents to combat human diseases caused by viral and bacterial pathogens.

Oligonucleotide products have been generated in a number of different ways including both organic synthesis techniques and traditional cloning procedures. Organic synthesis techniques have been optimized to achieve moderate quantities of oligonucleotides. These synthetic methods include techniques referred to as the di-ester, the tri-ester, the H-phosphonate, and the phosphoramidite methodologies, with the solid support synthesis of oligonucleotides by the phosphoramidite method being the most widely employed. A review of current methods of oligonucleotide synthesis is provided in Caruthers, ch. 1, *Oligonucleotides, Antisense Inhibitors of Gene Expression*, ed., Cohen, CRC Press, Inc., Boca Rotan, Fla. (1989). Currently available technologies and instrumentation are, however, still limited with respect to the quantities of the synthetic oligonucleotide products that can be generated. In addition, the relatively harsh chemistries of these synthetic methods can produce a significant percentage of chemically altered oligonucleotides in the final product.

Because these chemical alterations represent relatively subtle changes, synthetic oligonucleotides are nevertheless suitable for many purposes. For example, the chemical alterations in synthetic oligonucleotides do not significantly interfere with hybridization, enabling these oligonucleotides to function effectively as DNA probes in most diagnostic applications. Similarly, in site directed mutagenesis, where entire colonies or plaques are derived from a single oligonucleotide incorporation, a biological screen is inherently provided for the desired mutation event.

However, certain applications require that a higher integrity product be employed to achieve optimal results. Chemical alteration typically becomes a problem where the oligonucleotides are used in an application which requires or induces recognition of the oligonucleotide by a biologically active substance, most typically an enzyme. For example, oligonucleotide integrity becomes an issue in gene assembly where polymerase and ligase recognition of the oligonucleotide is required for cloning. This problem is particularly acute in the assembly of longer genes, because the opportunity for error to arise from chemical alteration increases proportionately with the length of the gene.

The issue of oligonucleotide integrity is even more problematic in a therapeutic application where the therapeutic oligonucleotide must interact with a variety of biologically active components in the patient's body. Further, any degree of incomplete deprotection or chemical modification in the therapeutic oligonucleotide product might trigger an immune response, or worse, impart a cytotoxic effect to the patient. It is therefore questionable whether synthetic oligonucleotides can be effectively employed as therapeutic agents. This problem is further exacerbated by the fact that the exact nature of these subtle changes or errors are difficult, if not impossible, to characterize by current methods of chemical analysis. Mandecki et al, *Biotechniques*, 9(1), 56–59 (1990).

Traditional cloning techniques provide an alternative method for producing oligonucleotides. In cloning, the desired oligonucleotide sequence is inserted into an appropriate vector which is subsequently used to transform a host cell which, as it grows, amplifies the inserted oligonucleotide. The oligonucleotide can be synthesized in vitro and then inserted into a vector which is amplified by growth, as disclosed in U.S. Pat. No. 4,293,652. The inserted oligonucleotide sequence, if appropriately designed, can then be excised, for example by cutting with a restriction enzyme, and subsequently purified from extraneous plasmid DNA by standard techniques.

Oligonucleotides generated by cloning do not carry the danger of chemical modification. As a result, these oligonucleotide products appear as native, or "wild type", oligonucleotides which will, for example, be recognized by enzymes. Cloning procedures, however, do not tend to be economical or amenable to large scale production of oligonucleotides. Because the inserted oligonucleotide sequence represents only a small portion of the plasmid sequence, the weight yield of product DNA is very small compared with the weight yield of the plasmid. Even the insertion of tandem repeats of the desired oligonucleotide sequence is likely to be of no avail in improving yield, because biological host cell systems typically excise tandem repeats during growth.

Target amplification, a technique which has been employed to improve sensitivity in probe diagnostics, provides yet another, albeit "untraditional", type of oligonucleotide synthesis. For example, U.S. Pat. Nos. 4,683,195 and 4,683,202 disclose a process known as polymerase chain reaction (PCR), wherein two oligonucleotide primers are employed such that the primers are complementary to the ends of different portions on opposite strands of a section of the target sequence. Following hybridization of these primers to the target, extension products complementary to the target sequence are formed in the presence of DNA polymerase and an excess of nucleoside triphosphates. The primers are oriented so that DNA synthesis by the polymerase proceeds across and through the region between the primers. The hybridized extension product is then denatured from the target and the cycle repeated, with extension product also acting as template for the formation of additional extension product in subsequent cycles of amplification. Each successive cycle theoretically doubles the amount of nucleic acid synthesized in the previous cycle, resulting in exponential accumulation of amplified product.

The PCR technology has been suggested for use as a method to achieve the production of large quantities of oligonucleotides, in European Patent Application No. 359, 545. PCR production of oligonucleotides is, however, still limited with respect to the quantity of final oligonucleotide product which can be generated by this method, because a stoichiometric amount of each synthetic oligonucleotide primer must be incorporated into each PCR extension product. (In reality, a large excess of these primers is required to drive the kinetics of the PCR reaction forward.)

Another drawback, most typically in therapeutic applications, lies in the inability of PCR to completely eliminate the nucleic acid integrity problems of organic synthesis, because the synthetic primers in fact become a portion of the PCR-amplified oligonucleotide. As a result, the primer-derived portion of the product will contain the same errors that compromise the quality of synthetic oligonucleotides. For this reason, PCR amplification products cannot be of significantly higher quality than than that of the starting oligonucleotide primers. Additionally, the Thermus aquaticus (Taq) DNA polymerase enzyme which is typically used in PCR amplifications is believed to add one or more nucleotides during amplification onto the 3'-ends of the products beyond the oligonucleotide primers. Denney et al, *Amplifications, A forum for PCR users*, 4, 25–26 (March, 1990). It is also believed that Taq DNA polymerase can add bases onto the 3'-end of oligonucleotides in solution. Denney et al, ibid. This would result in a product which is not sequence specific.

Other types of target amplification which have been developed for diagnostic applications also warrant mention. International Patent Application No. 89/02649 discloses a type of amplification procedure generally referred to as ligase chain reaction (LCR), wherein presynthesized pairs of amplification probes which hybridize contiguously to a section of the target sequence are ligated to form the complementary amplification product. As with PCR, the completed amplification product is separated from the target by heat denaturation, and the process repeated with both the target and amplification product acting as a template in subsequent cycles. The primary advantage of the LCR method over prior organic synthesis methods lies in its ability to generate longer oligonucleotides from the shorter presynthesized amplification probes. The final oligonucleotide product can be synthetic, wild type, or a combination of both, depending upon the composition of the presynthesized probes.

Yet another type of diagnostic amplification method, referred to as catalytic hybridization amplification ("CHA"), is disclosed in International Patent Application No. 89/09284. In this method, multiple copies of the complement of a portion of a target sequence are "generated" from the target-catalyzed cleavage of longer presynthesized complementary probe sequences. Cleavage of the longer probes occurs only where the target hybridizes to one of an excess of these complementary detection probes in such a way that the target sequence catalyzes selective cleavage of only that complementary probe. Because the target remains intact, it can be recycled through the reaction, enabling it to react with more than one of the complementary detection probes, thus leading to a large amplification of signal through proliferation of the shorter cleaved pieces. CHA reactions, however, fail to provide an advantage in the synthesis of oligonucleotide products, because longer presynthesized oligonucleotides are simply being cleaved into smaller pieces.

It is an object of the present invention to provide a cost efficient method for producing large quantities of high quality oligonucleotides.

It is a further object of the present invention to provide a method for producing large quantities of oligonucleotides that can be useful in a diagnostic setting.

SUMMARY OF THE INVENTION

The present invention uses a specially designed template sequence, otherwise referred to as a "substrate reagent", to catalytically assemble sequence specific oligonucleotide products from individual nucleoside triphosphate reagents in the presence of a polymerase and a cutting agent. Because the process is catalytic with respect to the template sequence, a virtually unlimited amount of product can be generated from a single molecule of template. A cascade can be formed from a series of these substrate reagent templates, wherein the nucleic acid product from one substrate reagent template catalyzes a synthesis reaction using the next substrate reagent in the series. Where the process is initiated by the presence of a target nucleic acid sequence, the method of the present invention can be used as an amplification method to improve sensitivity in a diagnostic setting. The catalytic synthesis of oligonucleotides can conveniently be made to proceed isothermally, even where a cascade is employed.

DETAILED DESCRIPTION OF THE INVENTION

Figure 1:
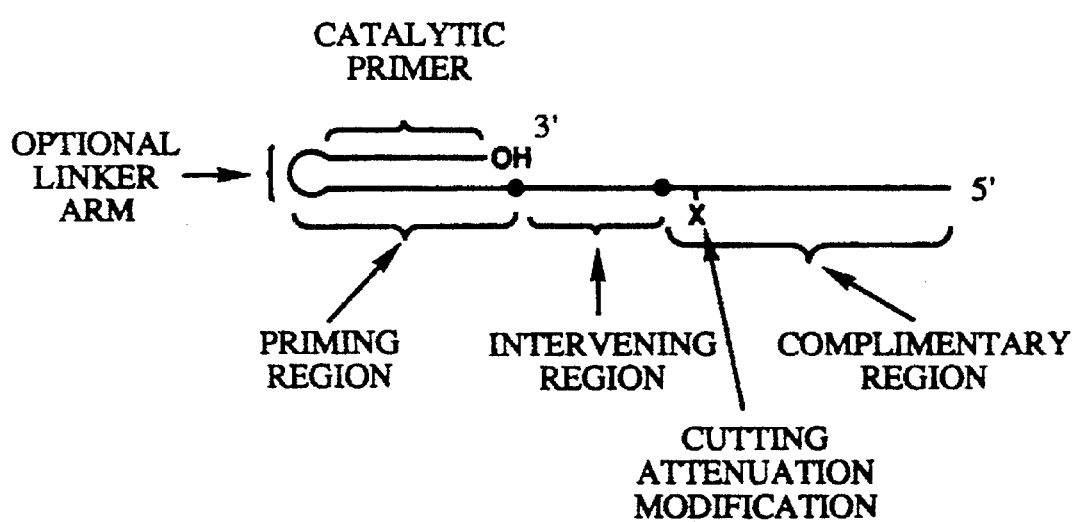
FIG. 1 illustrates the elements of a substrate reagent of the present invention.

The present invention provides a method for the catalytic assembly of sequence specific oligonucleotide products from a specially designed template in the presence of a polymerizing agent, an excess of monomeric nucleoside triphosphates, and a cutting agent. A substrate reagent is provided in the form of a modified template sequence. A cutting attenuation modification to the template sequence imparts resistance to cutting by a selected cutting agent, such as a restriction enzyme. The cutting attenuation modification enables the substrate reagent to remain intact following selective cleavage to generate the desired oligonucleotide. In this way, the substrate reagent can act as template for the in situ synthesis of the desired oligonucleotide over and over again.

The catalytic process of the present invention enables the production of an almost unlimited amount of oligonucleotide product from a single substrate reagent template. The product produced from the substrate reagent is of a native, or "wild type", quality because it is derived from "native" nucleoside triphosphates (dNTP's) and a DNA polymerase. Moreover, a series of substrate reagents can be employed to form a series of levels within a cascade to isothermally generate product. In the cascade, the product from the first level catalyzes the generation of product at the second level, and so forth. This results in an exponential accumulation of product, and is particularly useful in a diagnostic setting where the presence of target is used to initiate the cascade.

In order to more clearly understand the invention, it will be useful to set forth the definitions of certain terms that will be used herein:

Nucleic Acid Sequence or Oligonucleotide is a deoxyribonucleotide or a ribonucleotide which may be modified with respect to: (1) the phosphate backbone; (2) the nucleosides; and/or, (3) the ribose, or sugar moiety of the oligonucleotide. Nucleic Acid Sequences may contain labels or other attached moieties and can be interrupted by the presence of still other moieties, as long as hybridization can occur.

Substrate Reagent is a nucleic acid sequence template which has a cutting attenuation modification. When primed by the hybridization of a complementary catalytic primer to form a partial duplex, the Substrate Reagent acts as a template for the in situ synthesis of an extended substrate reagent. The Substrate Reagent may be pre-primed.

Cutting Attenuation Modification is a modification to the substrate reagent which will cause a cutting agent to selectively cleave the desired oligonucleotide cleavage product from an extended substrate reagent without cutting the substrate reagent template.

Selective Cleavage means that substantially only one strand of a duplex nucleic acid sequence is cleaved, although cleavage of both strands may occur to some extent.

Cutting Attenuation Efficiency is a measure of the degree to which the cutting attenuation modification prevents cleavage of the substrate reagent template during selective cleavage of the extended substrate reagent. The Cutting Attenuation Efficiency represents the proportion of modified nucleic acid sequence which remains intact following contact with a cutting agent through one cycle of extension and selective cleavage of a substrate reagent.

Catalytic Primer as used herein refers to a nucleic acid sequence which is complementary to a portion of a substrate reagent at or near the 3'-end of the substrate reagent and which is capable of priming the substrate reagent by acting as a point of initiation for the synthesis of an extended substrate reagent using the unhybridized single-stranded remainder of the primed substrate reagent as a template for polymerase extension.

Primed Substrate Reagent as used herein means a substrate reagent to which a catalytic primer has hybridized.

Pre-primed means the catalytic primer is provided in the reaction mixture as a presynthesized reagent.

Extended Substrate Reagent is the duplex product which is generated from the extension of a primed substrate reagent or an activated substrate reagent in the presence of an excess of nucleoside triphosphates and an agent for polymerization such as DNA polymerase. The Extended Substrate Reagent is extended substantially the entire length of the substrate reagent.

Cleavage Product is the single-stranded polymerase extended oligonucleotide product which is released by partial denaturation of a selectively cleaved extended substrate reagent.

Partial Denaturation refers to the denaturation of a portion of a selectively cleaved duplex. Partial Denaturation may, for example, refer to the release of a cleavage product from an extended substrate reagent which has been selectively cleaved. Partial Denaturation may also describe the denaturation of a portion of target sequence from a substrate reagent-target duplex during target initiation.

Activated Substrate Reagent is the partial duplex product which remains following partial denaturation of a selectively cleaved extended substrate reagent to release a cleavage product.

Partial Duplex may refer to either or both a primed substrate reagent and/or an activated substrate reagent.

Intervening Region is an optional portion of a substrate reagent which lies between the priming region and the complementary region. The Intervening Region may also be referred to as a Locking Region, because it can serve to "lock" the catalytic primer in place.

Cutting Agent is a chemically or biologically active substance, such as a restriction endonuclease, which selectively cleaves double-stranded nucleic acid sequences. Typically, the Cutting Agent selectively cleaves extended substrate reagent (leaving the substrate reagent template sequence intact) to generate cleavage product and an activated substrate reagent. The Cutting Agent may also selectively cleave the target portion of a substrate reagent-target duplex during target initiation.

Recognition Site as used herein means the specific sequence recognized by an enzyme, such as a restriction endonuclease.

Enzyme Cleavage Site means the phosphodiester bond which is hydrolyzed by an enzyme, such as a restriction endonuclease.

Remote Cutting Restriction Endonuclease, or Remote Cutter, is a restriction endonuclease that cleaves double-stranded DNA at a site outside of the enzyme recognition site.

Restriction Site may refer to both the recognition site and the enzyme cleavage site for a non-remote cutting restriction enzyme.

Cascade refers a series of substrate reagents wherein the cleavage product from one substrate reagent catalyzes, or primes, the next substrate reagent in the series. The first substrate reagent in the series must be pre-primed.

First Level refers to the first in a series of substrate reagents which form a cascade.

Higher Level refers to any substrate reagent other than the first in a series of substrate reagents which form a cascade.

Amplify or Amplification means to generate a greater quantity of final oligonucleotide product than starting oligonucleotide, such as target, through the catalytic action of at least one primed or activated substrate reagent.

Amplification Cascade as used herein refers to the situation where a cascade is employed to achieve amplification of a starting oligonucleotide sequence. In an Amplification Cascade, the first substrate reagent in the series is pre-primed through target initiation.

Target Initiation refers to target-induced in situ synthesis of a substrate reagent.

Target Sequence is the nucleotide sequence being sought in a particular assay.

Presynthesized nucleic acid sequence as used herein means an oligonucleotide sequence which has been synthesized prior to being added to a reaction mixture.

Complementary refers to sufficient complementarity to enable hybridization and/or extension to occur.

Complete complementarity is not required.

Catalytic Production of Oligonucleotides

The nucleic acid substrate reagent is central to the present invention. Although the exact composition of the substrate reagent will vary, depending upon the intended use of the final oligonucleotide cleavage product, the substrate reagent nevertheless contains a minimum of two regions. In most cases, the substrate reagent will contain at least three regions, as shown in FIG. 1. A first required region is complementary in sequence to the desired oligonucleotide product, and is referred to as the "complementary region". A second required region of the substrate reagent is complementary to at least a substantial portion of a catalytic primer which primes synthesis of the desired oligonucleotide sequence from a 3'-hydroxyl group using a polymerase and dNTP's, and is referred to as the "priming region". The complementary region and the priming region may be contiguous, or these regions may be separated by a third region referred to as an intervening region.

The priming region of the substrate reagent will typically be pre-primed for the synthesis of the desired oligonucleotide cleavage product. For example, the catalytic primer may be provided as a separate presynthesized reagent. In order to facilitate hybridization of the catalytic primer to the substrate reagent, both the catalytic primer and the substrate reagent may be introduced as a composite reagent with the catalytic primer already annealed to the priming region. Where the latter approach is taken, it may be convenient for the catalytic primer to be covalently attached to the priming region of the substrate reagent template, such as through a linker arm as shown in FIG. 1. It is most practical, and therefore preferred, that the linker arm be a nucleic acid sequence.

The substrate reagent will contain a cutting attenuation modification which allows for the selective cleavage of the synthesized oligonucleotide product from the extended substrate reagent. Because the cutting agent selectively cleaves only the polymerase extended strand of the extended substrate reagent, the substrate reagent template remains substantially intact. Preferably, the cutting attenuation modification will impart complete resistance to cutting. It is also acceptable, however, for the modification to attenuate cutting to a substantial, but less than complete, degree. Cutting attenuation efficiencies as low as 50% may function adequately in the method of the present invention, depending upon the particular substrate reagent design and desired end use of the oligonucleotide cleavage product.

It will be appreciated that loss of substrate reagent, due to cleavage of the substrate reagent from cutting attenuation efficiencies of less than 100%, will increase with each cycle, thus having a substantial effect on the overall efficiency of the system. For example, a cutting attenuation modification with 50% cutting attenuation efficiency will result in a loss of approximately 50% of the total amount of primed substrate reagent after the first cycle, 75% after the second cycle, and so forth. The loss of substrate reagent from lower cutting attenuation efficiencies is less critical where lesser amounts of final oligonucleotide cleavage product are desired, because fewer cycles of oligonucleotide production will be required to achieve the desired end result. The negative impact of low cutting efficiencies may also be overcome to some degree where the cascade format of the present invention is employed, as later described.

The cutting attenuation modification is important, because it enables the substrate reagent to be used over and over again, imparting the desired catalytic behavior to the system. For this reason, it is preferred that the cutting attenuation modification provide at least 60% cutting attenuation efficiency. It is more preferred that cutting attenuation efficiency be at least 90%. Most preferably, the cutting attenuation modification will provide a cutting attenuation efficiency of at least 95%. It is also preferred that the cutting attenuation modification not interfere significantly with polymerase activity across the substrate reagent template. It may be necessary to screen potential cutting attenuation modifications, as taught in the examples which follow, to identify an optimal cutting attenuation modification for a particular system.

As noted, a cutting agent is employed to effect the release of the synthesized oligonucleotide product from the extended substrate reagent. Like the catalytic primer, this agent can either be attached to the substrate reagent, or it can be provided separately. The cutting agent will generally be a chemically or biologically active substance. What is important in the selection of a cutting agent is that the cutting agent selectively cleave the desired oligonucleotide cleavage product from the extended substrate reagent while leaving the substrate reagent template sequence substantially intact. It will therefore be appreciated that the cutting attenuation modification and the cutting agent operate in tandem. A preferred cutting agent/cutting attenuation modification combination is a restriction endonuclease with a corresponding chemical modification in the substrate reagent backbone. In this case, the backbone modification renders the substrate reagent resistant to restriction endonuclease cleavage.

In addition to the preferred restriction enzyme cutting agent, sequence specific mammalian endonucleases, such as recombinases, can also act as cutting agents according to the present invention. These endonucleases are less well characterized than restriction enzymes, but can provide important advantages for the in vivo generation of oligonucleotide cleavage products.

It is further possible to use chemical means of cleavage as the cutting agent. For example, certain chelator-metal complexes have been tethered to oligonucleotide sequences on either the 3'- or 5'-ends to effect cleavage of a corresponding complementary nucleic acid strand. These chelator-metal complexes include: EDTA-Fe (Boutorin et al, *FEBS Lett.*, 172, 43–46 (1984)); phenanthroline-Cu (Chen et al, *J. Amer. Chem. Soc.*, 110, 6570–6572 (1988)); and porphyrin-Fe/Co/Mn (Le Doan et al, *Biochemistry*, 25, 6736–6739 (1986)). Cleavage of the complementary nucleic acids is induced through the production of the OH· radicals which result from a localized concentration of hydrogen peroxide produced by dismutation of superoxide anion $O_2^-$. The superoxide anion is produced spontaneously as a result of electron transfer from the metal to molecular oxygen.

These chelator-metal complexes are known to cause the cleavage of nucleic acids on the opposite strand of the tethered strand without attacking the tethered strand to which the chelator-metal complex is attached. The resistance of the tethered strand to the cutting action of the chelator-metal complexes is probably due to steric constraints imposed by the tether. In this case, the substrate reagent of the present invention would be labeled with the chelator-metal complex, which would then cut the upper strand of the extended substrate reagent. The cutting attenuation modification in this case is the tether, which not only attaches the complex to the substrate reagent, but which also causes the steric constraint(s).

The design of the substrate reagent is critical to its efficient use in the method of the present invention. Where presynthesized substrate precursors are used to form the substrate reagent, as in the case of target initiation described below, the design of these substrate precursors is also critical. Once designed, synthesis of the substrate reagent and/or substrate precursors can be performed according to any known technique. Many such techniques, including those described in the background of this patent application, are known to those skilled in the art. It is preferred that the integrity of the substrate reagent be as close to a naturally occurring oligonucleotide sequence as possible in order to facilitate recognition by a biologically active polymerase.

In designing the substrate reagent, the complementary portion of the substrate reagent is selected to be complementary to the desired oligonucleotide product. Theoretically, the method of the present invention can be used to generate cleavage products ranging in size from 1 to several thousand nucleotides in length. Preferably, where an isothermal process is employed, the oligonucleotide cleavage product will be no more than about 60 nucleotide bases in length. More preferably, the desired oligonucleotide cleavage product will also be at least about 6 to 12 nucleotide bases long. A length of approximately 6 bases or longer is generally required for oligonucleotides to function as linkers for cloning or for primers in polymerase extension reactions. Oligonucleotides of approximately 12 bases or longer are required for use as sequence specific probes for simple genomes such as *E. coli*. The upper limit of approximately 60 nucleotide bases is established for isothermal processes, because the melting temperatures ($T_m$) of longer oligonucleotide products converge upon the same value at or about this point. Thus, oligonucleotides longer than about 60 bases cannot be differentiated or selectively denatured by temperature adjustment(s). For example, the $T_m$ of a 60-mer oligonucleotide may be identical to that of a 100-mer oligonucleotide, making it difficult, if not impossible, to identify a temperature which will allow for the selective partial denaturation of a desired 60-mer oligonucleotide cleavage product while leaving a 100-mer catalytic primer hybridized to the substrate reagent template.

Within these limitations, the exact length of the complementary region, and corresponding cleavage product will be determined by the desired end use of the oligonucleotide cleavage product. Antisense oligonucleotides, for example, must be effective at physiological temperatures, and are typically about 15 to 25 nucleotides long. Generally, longer antisense oligonucleotides within this range are desirable, because they have a lower probability of occurring by chance in large genomes. For example, a 17-mer oligonucleotide should be unique to a mammalian genome. On the other hand, if an antisense oligonucleotide is too long (i.e., substantially longer than 25 nucleotides), it may hybridize nonspecifically to longer non-target sequences. This type of nonspecific hybridization is unavoidable, because the physiological body temperature of a patient cannot be adjusted to increase stringency.

Nonionic antisense oligonucleotides have a slightly higher $T_m$, due to the lack of phosphate charge repulsion, and will typically be selected at the shorter end of the 15 to 25 nucleotide range than will unaltered ionic oligonucleotides. Phosphorothioates and phosphorodithioates, on the other hand, have a slightly lower $T_m$. These oligonucleotides may be adjusted to be as much as 25 to 30 nucleotides long. It is possible to incorporate phosphorothioate linkages into DNA by polymerase extension in the presence of dNTPαS (2'-deoxynucleoside 5'-o-(1-thiotriphosphate)) and a suitable template. Eckstein et al, *Nuc. Acids Res.*, 13(24), 8749–8764 (1985). Many restriction endonucleases are able to cleave this modified phosphate internucleotide bond, and it therefore should be possible to produce phosphorothioate-containing cleavage products using the present invention. Furthermore, since only the $S_p$ optical isomer serves as a substrate for DNA polymerases, the resulting cleavage products will be optically pure.

The cleavage product of the present invention may also be used as an oligonucleotide probe or primer. In this case, the optimal size of the cleavage product will vary with respect to the intended assay configuration. Because the stringencies of an in vitro probe application can be adjusted, the range of potential probe sizes is far greater than that allowable for antisense oligonucleotides. Nevertheless, the probe or primer size should be adjusted to be unique with respect to the size of the genome in the analyte. For example, PCR probes are generally 15 to 35 base pairs in length, while LCR probes are typically 8 to 35 base pairs in length.

The priming and intervening regions of the substrate reagent can be any oligonucleotide sequence that is convenient for practical purposes. For example, it may be convenient for the priming region to be complementary to a readily available supply of oligonucleotide sequences, such as diagnostic probes or primers. It is further preferable that the priming region not be complementary to the complementary and/or intervening region(s) of the substrate reagent, as this can result in the substrate reagent folding back on itself. The catalytic primer will preferably have a higher $T_m$ than the oligonucleotide cleavage product, as this will aid in keeping the catalytic primer from melting off during denaturation to effect release of the cleavage product. This usually means that the priming region will be at least as long as the oligonucleotide cleavage product, particularly where the substrate reagent does not have a locking region. More preferably, the catalytic primer will be 1-5 bases longer than the cleavage product. Typically, a 8- to 9-mer oligonucleotide is sufficient to achieve priming.

Unlike the complementary region, which must be substantially the same length as its complementary cleavage product, it is not necessary that the priming region be substantially the same length as the complementary catalytic primer. For example, the 5'-end of the catalytic primer may extend beyond the 3'-end of the (priming region of) the substrate reagent, providing a "tailing sequence" on the catalytic primer. In fact, it may be beneficial in some cases to use the tailing sequence as a template for polymerase extension such that the substrate reagent acts as a primer for extension opposite the tailing sequence. It is also possible for the 3'-end of the substrate reagent to extend beyond the 5'-end of the catalytic primer, providing an optional "capping region" on the substrate reagent, as more fully described later.

Where an intervening region is part of the substrate reagent, greater flexibility is available in the selection of a catalytic primer. With an intervening region, the catalytic primer can actually be shorter than the cleavage product, because the added length provided by polymerase extension opposite the intervening region may be used to effectively "lock" this shorter catalytic primer onto the substrate reagent at a temperature which still allows for denaturation of the cleaved oligonucleotide product. Essentially, the catalytic primer will be an oligonucleotide having a sufficiently high $T_m$ to enable an appreciable degree of hybridization to the priming region of the substrate reagent. In this case, the polymerization reaction can begin quickly enough to lock the catalytic primer onto the substrate reagent. With an intervening region, the catalytic primer can be as much as several bases shorter than the cleavage product. In any event, the total length of the priming region plus intervening region will preferably be at least as long as the cleavage product.

The cutting attenuation modification may be located within any of the regions of the substrate reagent depending upon the particular design of the system. The precise location of the cutting attenuation modification will vary with respect to the exact cutting attenuation modification and cutting agent selected. Optimal positioning of the modification will be apparent to one of ordinary skill in the art through minimal experimentation following the teachings of the present invention. Incorporation of the selected cutting attenuation modification into the substrate reagent will generally be made through the use of an appropriately modified nucleotide, ribose, or phosphate at a preselected point during synthesis of the substrate reagent.

Figure 2:
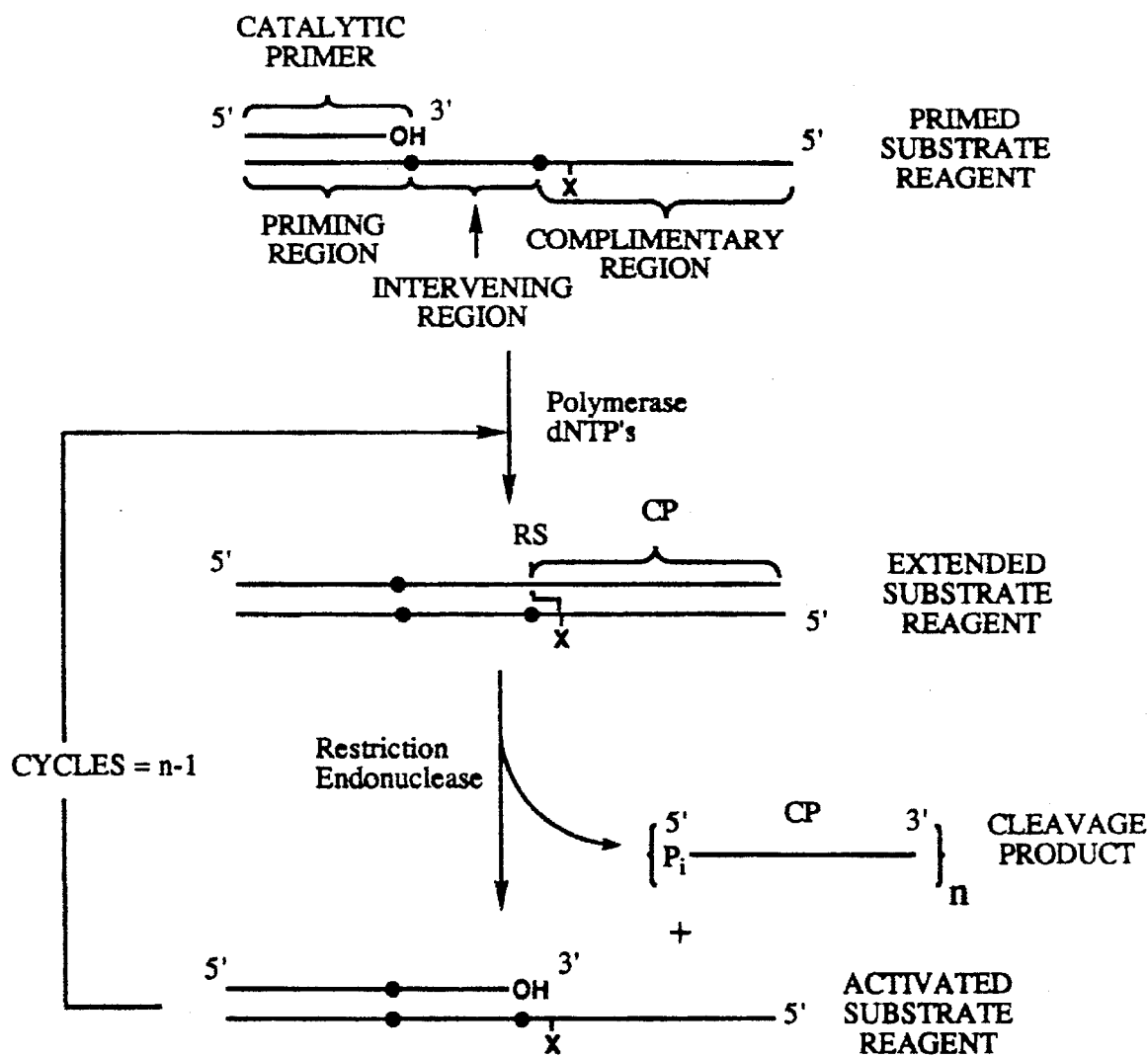
FIG. 2 demonstrates the in situ synthesis of an oligonucleotide sequence from a substrate reagent of the present invention.

The substrate reagent is provided in a reaction mixture with the corresponding catalytic primer and cutting agent, an agent for polymerization, and an excess of dNTP's. All of the reagents may be provided initially. Sequential addition is unnecessary. FIG. 2 demonstrates the synthesis of an oligonucleotide cleavage product from a pre-primed substrate reagent which does not contain the optional linker arm of the present invention. The pre-primed substrate reagent shown in FIG. 2 contains an intervening region between the priming region and the complementary region. The cutting attenuation modification of the substrate reagent in FIG. 2 is provided in the form of a backbone modification located within the complimentary region of the substrate reagent, with the cutting agent being provided as a corresponding restriction endonuclease. The primed substrate reagent is contacted with a DNA polymerase and an excess of dNTP's, which results in extension through the intervening sequence and the complementary region to create an extended substrate reagent. Formation of the extension product necessarily generates a restriction endonuclease recognition site on the extended upper strand near the cutting attenuation modification site.

As shown in FIG. 2, contacting the extended substrate reagent with the appropriate corresponding restriction endonuclease results in cleavage of the internucleotide bold which covalently binds the desired oligonucleotide product (CP) to the remainder of the extended portion of the extended substrate reagent. The corresponding cutting attenuation modification on the substrate reagent template, however, impedes concurrent cutting of the complementary template strand. The action of the cutting agent leaves the desired oligonucleotide product bound to the remainder of the extended substrate reagent only by hydrogen bonding with the strand. The reaction mixture can therefore be held at a temperature at or near the $T_m$ of the desired oligonucleotide cleavage product to effect release of this cleavage product.

The action of the cutting agent and subsequent denaturation of cleavage product from the substrate reagent template also generates an activated substrate reagent which can again be extended by polymerase action with an excess of dNTP's to regenerate the extended substrate reagent for another cycle of oligonucleotide synthesis. The activated substrate reagent differs from the primed substrate reagent in the number of individual nucleoside bases which must be added by extension to generate extended substrate reagent. The activated substrate reagent is referred to as "activated", rather than "primed", because it requires addition of only the bases that will make up the resulting cleavage product in order to generate another copy of cleavage product. If there is no intervening region between the priming region and the complementary region, the primed substrate reagent and activated substrate reagent will be identical.

In the presence of a polymerase and dNTP's, the activated substrate reagent will regenerate the extended substrate reagent, leading to yet another copy of the desired oligonucleotide cleavage product (CP from FIG. 2) following cleavage by the selected cutting agent. Importantly, all of these processes can occur rapidly in the same reaction mixture without the need for thermocycling or the addition of fresh reagents. The net result of this process is the repetitive catalytic conversion of dNTP's into the desired oligonucleotide cleavage product under isothermal conditions. (It should be noted that oligonucleotides produced by this process will typically be phosphorylated on their 5'-ends, depending upon the particular restriction enzyme used as the cutting agent.)

One of the advantages of the method of the present invention is the relative cost savings achievable by generating oligonucleotide products by this enzymatic means as compared with conventional organic synthesis methods. The cost savings are of particular benefit in the area of oligonucleotide therapy, where gram quantities of material are projected to be required for a single therapeutic dose. Although the commercial cost of the dNTP reagents required by the present method can be more expensive than the amidite reagents required by traditional organic synthesis methodologies, this higher cost is more than offset when the relative efficiency of the amidite technologies is factored into the comparison. Specifically, the phosphoramidite synthesis technologies require a large excess of non-reusable reagents to insure high condensation efficiencies, whereas nearly all of the more expensive dNTP's can be converted to product using the present method, making the overall cost of nucleoside reagents for the method of the present invention considerably less than that of conventional methodologies. Moreover, a considerable portion of the expense of the dNTP reagents lies in the fact that these reagents are commercially available only as separate dATP, dTTP, dCTP, and dGTP reagents. The present method, however, employs a mixture of these dNTP's. Thus, a commercial source of a combined reagent containing all four dNTP's could reduce the cost of reagents for the method of the present invention by as much as an order of magnitude, because the cost of separating the dNTP's could be eliminated.

It is possible to use a mixture of all four dNTP's in the present method, because the template provided by the substrate reagent performs the task of selecting the appropriate dNTP from the dNTP pool to achieve the desired sequence of the finished oligonucleotide cleavage product. With current organic synthesis methods, this selection must be done manually or by programming an automated sequenator, requiring that separate reagents be added in a step-by-step manner to achieve the desired end product. This enables the method of the present invention to generate the desired large quantities of oligonucleotide product with much greater speed than conventional methodologies.

Just as important as the cost and output advantages achievable by the enzymatic method of the present invention, is the high integrity of the oligonucleotide product that is produced in this manner. Therapeutic oligonucleotides generated enzymatically according to the present invention are of native quality and are, therefore, more likely to be suitable for administration to a patient than are the synthetic oligonucleotides derived from traditional organic synthesis techniques. The preference for wild type products lies in the lower probability of these products to induce and immunogenicity and cytotoxicity reactions. Also, while racemic mixtures of optically active products, such as phosphorothioates, are formed according to traditional synthesis procedures, it is possible to obtain optically pure preparations of these modified oligonucleotide products for therapeutic use by the method of the present invention, as noted below.

Although cleavage products of wild type DNA (containing phosphate bonds) are acceptable and desired for most applications, it is also possible to incorporate modified nucleotides into the cleavage product using modified nucleoside triphosphates, provided these modified dNTP's do not interfere with polymerase extension. For example, biotinylated nucleosides and/or nucleosides containing amine groups can be incorporated into DNA by polymerase using the desired modified dNTP(s). Ward et al, *Proc. Natl. Acad. Sci. USA*, 78(11), 6633–6637 (1981). The modification(s) can be made to the final oligonucleotide product in this manner using a dNTP pool wherein one, two, three, or all four of the dATP, dTTP, dCTP, and dGTP reagents are modified. Phosphorothioate internucleotide bonds have also been created using polymerase and dNTPαS. Eckstein et al, ibid. In this case, only one of the two possible diastereomers serves as a substrate for polymerase. It is therefore possible to do stereoselective synthesis using the method of the present invention. For example, chemical synthesis of a 20-mer oligonucleotide containing phosphorothioate linkages, using racemic starting materials, will yield over 1,000,000 isomers. On the other hand, the method of the present invention will yield only one optically pure isomer.

Modified oligonucleotides may be preferred in some antisense applications. It may also be possible to generate, through the incorporation of modified nucleosides, an oligonucleotide cleavage product that can itself serve as a substrate reagent. In other words, the modified nucleosides could be used to incorporate a cutting attenuation modification into the cleavage product. In the presence of an appropriate catalytic primer, this cleavage product could then serve as a substrate reagent to generate its own cleavage product.

In vivo Production of Oligonucleotides

The catalytic method of the present invention is also adaptable for the in vivo, or intracellular, production of oligonucleotides from a primed substrate reagent. This in vivo reaction has potential for enabling the production of antisense oligonucleotides directly in the cells of the patient or directly in bacterial cells residing within the patient. In order to achieve this type of result, the appropriate primed or activated substrate reagent could be provided directly to a patient, such as in the form of an injectable therapeutic. Once inside the cells within the patient's body, the substrate reagent could then catalytically generate the desired antisense oligonucleotide. The catalytic reaction would, of course have to occur isothermally at the patient's body temperature.

Because only a catalytic amount of the substrate reagent is required to generate a correspondingly high level of antisense oligonucleotide, the dose required for therapeutic action could be reduced significantly (e.g., from gram to milligram quantities). Not only would this reduce the cost of antisense therapy to a practical level, but it would also reduce the potential for immunogenicity reactions which are more likely to result from the introduction of large amounts of a foreign therapeutic into a patient. In other words, the required "large amount" of therapeutic cleavage product would be formed in the cell and would, therefore, necessarily be of native quality. There is also a measure of convenience and patient comfort achievable from the administration of milligram amounts of therapeutic through a single injection, rather than gram amounts through intravenous infusion.

The method of the present invention is particularly well suited for this in vivo application, because endogenous polymerases and deoxyribonucleoside triphosphates are available in the desired target cell to support the intracellular synthesis of the desired antisense oligonucleotide products. Target cells for the substrate reagent therapeutic may include normal cells in the patient, as well as abnormal cells (e.g., virally infected) or bacterial cells which have invaded the patient's body. Many of these cells also carry endogenous sequence specific endonucleases which would be available to serve as cutting agent(s) for appropriately designed substrate reagents. For example, most bacterial strains carry restriction endonucleases which could be used as the cutting agent. In this case, intracellular production of an antisense oligonucleotide could produce a desired cytotoxic effect, thus having potential applicability as an antimicrobial therapeutic.

It is even conceivable that the presence of a particular target nucleic acid sequence in a cell could serve to assemble substrate precursors into an activated or primed substrate reagent. This "target-initiated" substrate reagent could produce multiple copies of, for example, an antisense oligonucleotide that imparts a desired cytotoxic effect. In this case, cells containing a particular target sequence such as the human immunodeficiency virus could be selectively destroyed by cytotoxic antisense oligonucleotides produced as a result of the target initiation phenomenon more fully described below.

Although mammalian cell lines are less well characterized than microbial cell lines, the former are also known to carry sequence specific endonucleases that are required for recombination events. For example, "stuffer" sequences located between a 7-mer and a 9-mer of defined sequence in the RSS sequence of immunoglobulin genes and in T-cell receptor gene rearrangements have been observed to recombine in certain lymphoid cells. The "stuffer" region can be of any sequence, and could therefore serve as the cleavage product according to the present invention. ICSU Short Reports; Advances in Gene Technology, *Proceedings of the* 1990 *Miami Biotechnology Winter Symposia,* 10, 21 (1990). These recombination events require double-strand cleavage by a recombinase at the sites which are flanked by the sequence specific 7-mer and 9-mer. In an in vivo application of the present invention, this same recombinase could serve as the cutting agent for a substrate reagent therapeutic, provided the primed substrate reagent also contained two cutting attenuation modifications at the junctions of the stuffer sequence to prevent cutting of the substrate reagent template. In cases where a particular cell does not carry a sequence specific endonuclease, the cutting agent could be tethered to the primed substrate reagent or to the appropriate substrate precursors from which it is derived.

Target Initiation

The catalytic oligonucleotide production method of the present invention can be initiated by the presence of a target. The primary advantage of target initiation is to enable oligonucleotide synthesis to be used for diagnostic purposes as a method for amplification in response to target sequence in a patient test sample. Target initiation can, however, provide other significant benefits, such as in the in vivo applications discussed above.

Target initiation requires that the target induce, or trigger, the in situ synthesis of a substrate reagent. This target-initiated substrate reagent can be single-stranded or it can be a partial duplex in the form of either a primed substrate reagent or an activated substrate reagent. If the in situ-synthesized substrate reagent is single-stranded, a catalytic primer must be provided as an additional reagent. It is therefore preferred that the initiation process result in a substrate reagent which is a partial duplex. Initiation can take place in any one of a number of ways. Initiation methods can be isothermal, or they may require thermocycling. There are advantages to both types of methods, as will be discussed. In any event, it is preferred that the target sequence initiate amplification by acting as a template to catalyze the in situ synthesis of a substrate reagent. In this case, it is convenient to use presynthesized nucleic acid sequences, referred to as substrate precursor(s), to effect initiation.

Figure 3:
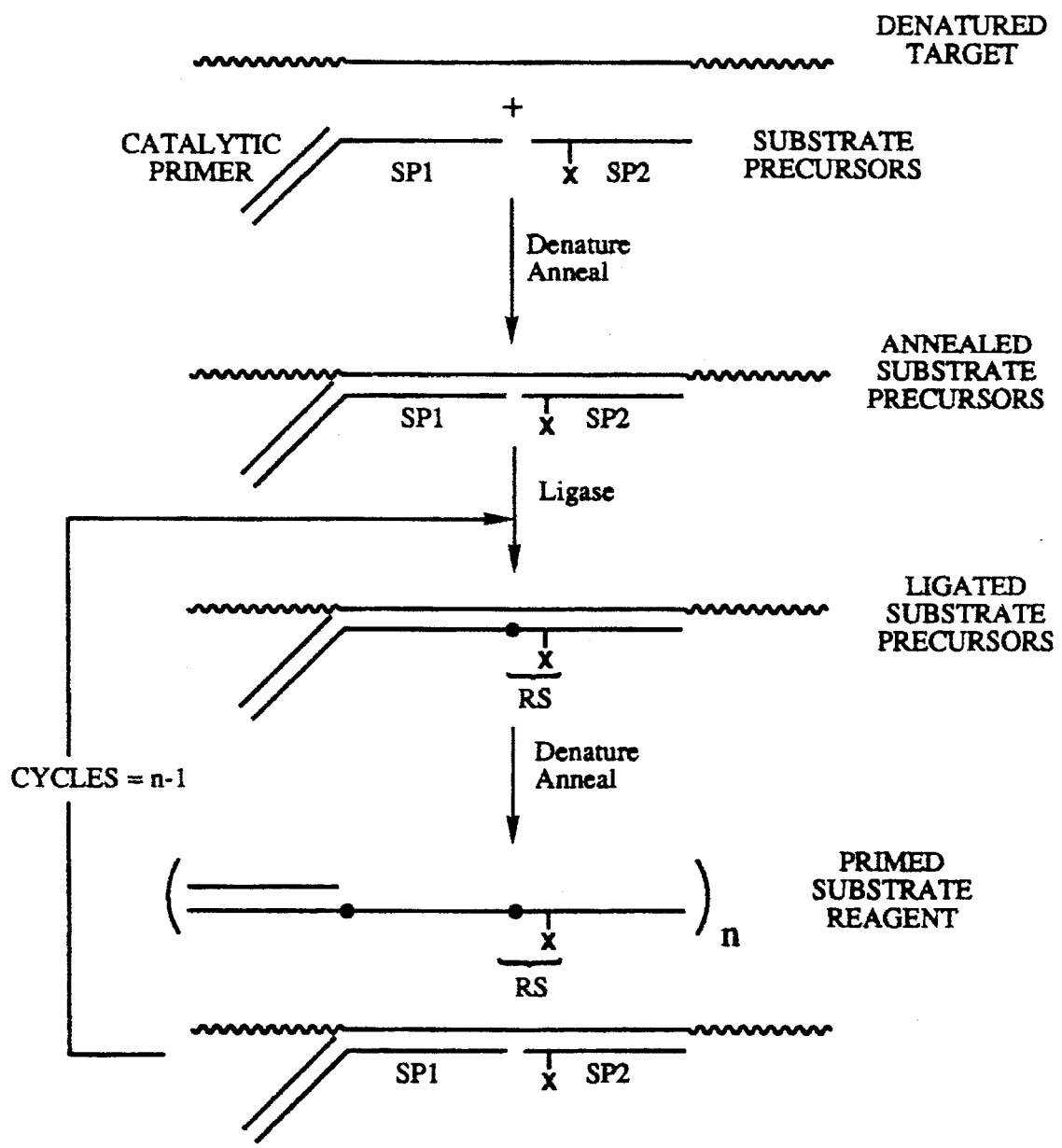
FIG. 3 is an example of a "self-priming" method of target initiation scheme wherein the target acts as a ligation template for two contiguously hybridizing substrate precursors.

The target sequence can act as a "ligation template" for the contiguous hybridization and subsequent ligation of two or more substrate precursors to form the complete substrate reagent. It will generally be preferred to use two substrate precursors in ligation template target initiation. In any event, the ligation template method of target initiation may be "self-priming" or "target-priming", as described below, either of which may be preferred, depending upon whether thermocycling is viewed as a disadvantage in a particular application of target initiation.

Where the self-priming embodiment is used, one of the substrate precursors is synthesized so that it provides the catalytic primer for the completed substrate reagent. For example, in the self-priming method of ligation template target initiation shown in FIG. 3, one of the substrate precursors $SP_1$ contains a sequence which is complementary to a portion of the target sequence and an additional non-complementary (priming region) sequence which is hydrogen bonded to the catalytic primer for the substrate reagent. The other substrate precursor $SP_2$ is complementary to a contiguous portion of the target sequence next to the non-priming end of $SP_1$. The cutting attenuation modification is preferably located on one of the substrate precursors at a position selected to achieve the appropriate cutting by the cutting agent in the eventual oligonucleotide synthesis scheme.

Where a target is double-stranded, the target-containing sample must first be denatured before it can anneal with the substrate precursors. Denaturation may take place in the presence of an excess of the substrate precursors, with annealing of the substrate precursors also taking place at a temperature dictated by the lower $T_m$ of the two substrate precursors. Once annealed, the two contiguously hybridized substrate precursors can be ligated to form a self-primed substrate reagent. In this type of target initiation, a separate heating step is required to release the completed substrate reagent. It is important to provide a large excess of the substrate precursors, as this not only drives the reaction forward, but also provides an excess of catalytic primer provided by the non-complementary region of $SP_1$, so that if catalytic primer is melted off during denaturation, the substrate reagent will quickly be re-primed from the excess of reagents provided. This process has the advantage that it can be repeated with thermal cycling to generate additional copies of the substrate reagent, as shown in FIG. 3.

Figure 4:
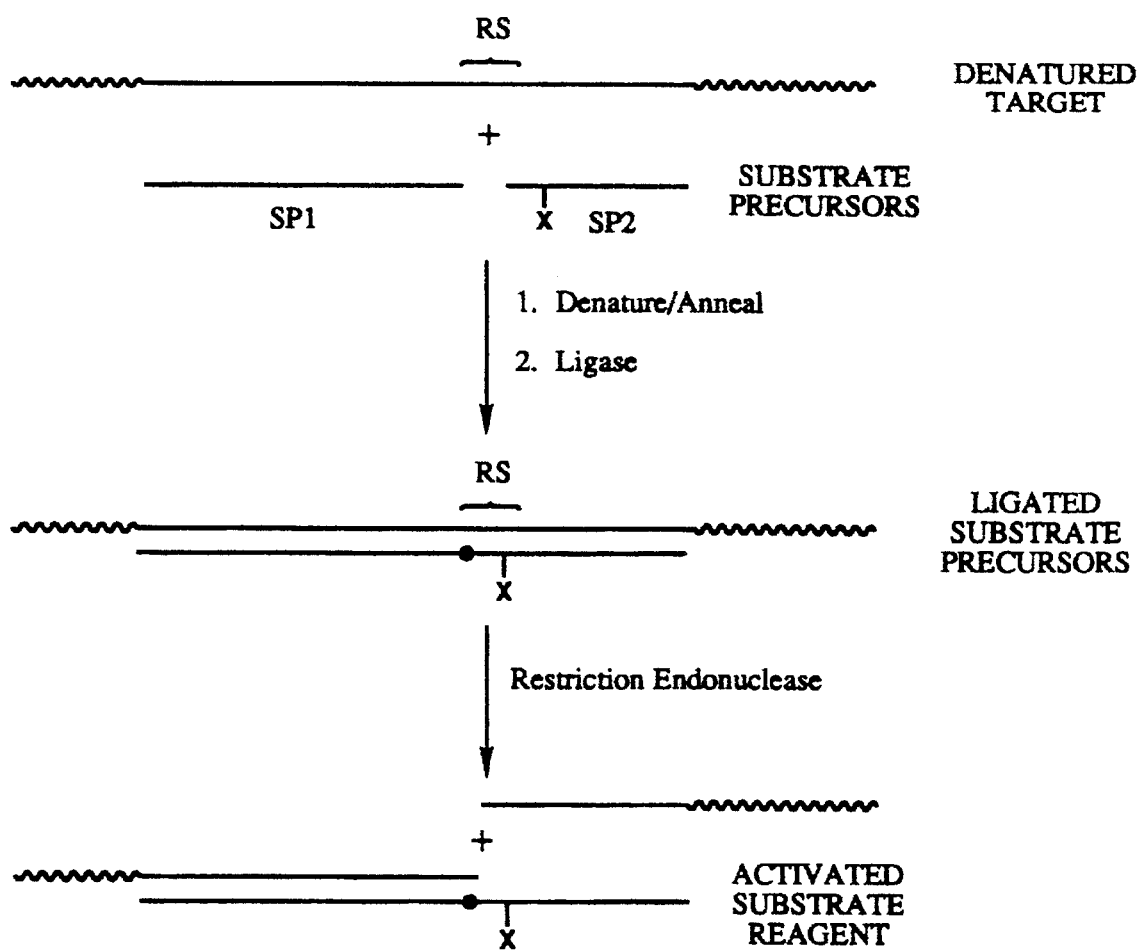
FIG. 4 is an example of a "target-priming" method of target initiation scheme wherein the target acts as a ligation template for two contiguously hybridizing substrate precursors.

In a target-priming type of ligation template target initiation, the target not only acts as a ligation template for the substrate precursors, but also provides the catalytic primer necessary to form the primed or activated substrate reagent. The target-primed initiation embodiment offers the advantage that once sample target DNA is denatured, the remainder of the initiation process is isothermal. The disadvantage to this method is that only one copy of primed substrate reagent is produced from each target sequence. Unlike the self-priming embodiment, $SP_1$ does not carry a separate catalytic primer region, as shown in FIG. 4.

In both the self-primed and target-primed ligation template initiation embodiment, the substrate precursors are preferably designed so that a ligation event is required to generate a complete restriction site. The cutting attenuation modification, positioned on $SP_1$ and/or $SP_2$, prevents cutting of the assembled substrate reagent. In the target-primed ligation method of target initiation shown in FIG. 4, activated substrate reagent is formed by selective cleavage of the target strand, through the action of a cutting agent such as a restriction endonuclease. This cutting agent is preferably the same cutting agent used to selectively cleave extended substrate reagent in the ensuing oligonucleotide production method.

In the case of target-primed initiation, it is preferred that the intact substrate reagent be released isothermally from the cleaved target through partial denaturation. This result can be achieved in the target-primed embodiment through initial temperature adjustment of the initiation reaction so that only that portion of the cleaved target which is hybridized to the complementary region of the completed substrate reagent denatures from the substrate reagent, releasing an activated substrate reagent. Isothermal denaturation avoids the need for the separate heating step required to effect release of the assembled substrate reagent in the self-priming method. Although it is important that the remainder of the target, which primes the activated substrate reagent, remain hybridized during denaturation of the cleaved target portion from the complementary region, this result can also be easily achieved by adjusting the $T_m$ of this portion of the partial duplex through the use of a longer substrate precursor $SP_1$.

Figure 5:
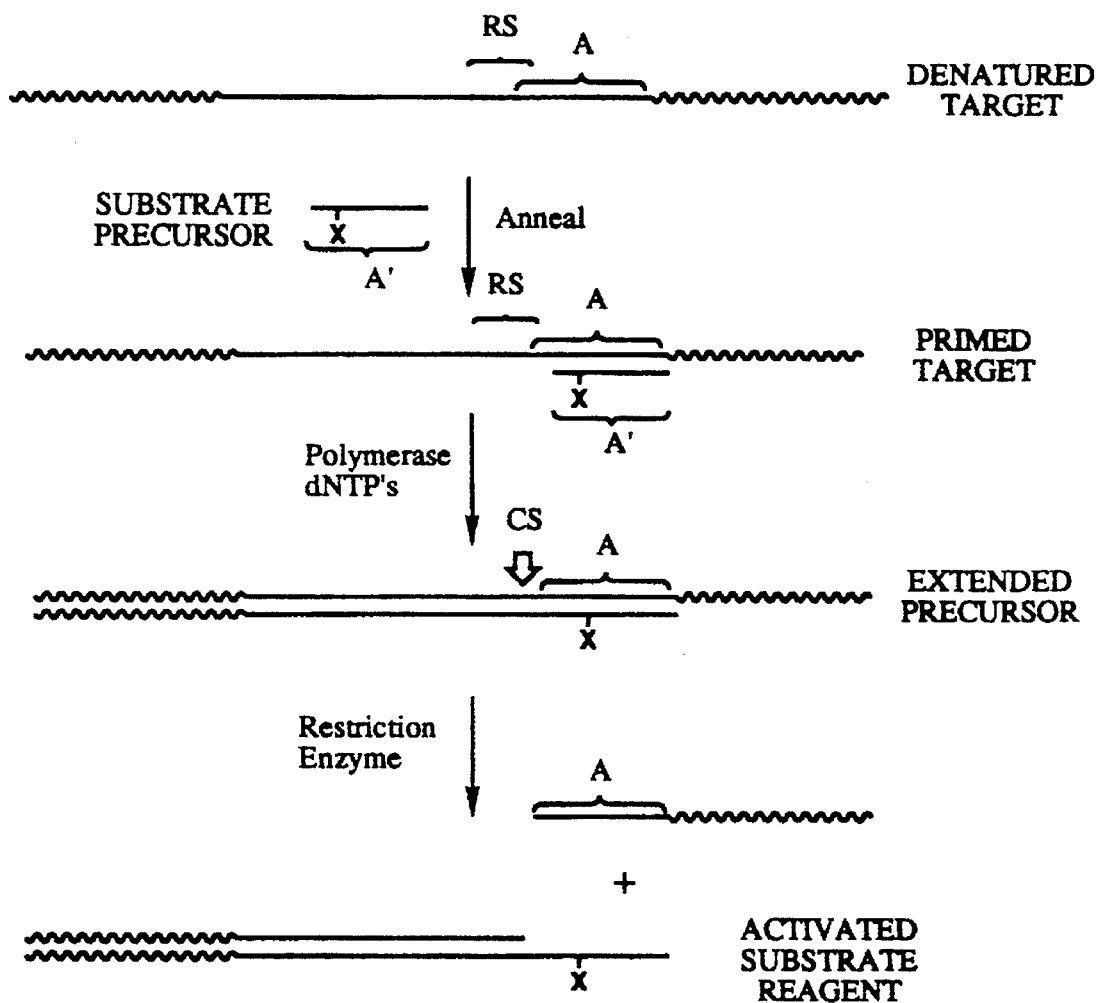
FIG. 5 is an example of "target-priming" method of target initiation scheme wherein the target acts as a polymerization template for a single priming substrate precursors.

It is more preferred, however, to initiate amplification by using the target sequence as a polymerization template for a single substrate precursor which primes extension opposite the target. In the polymerization template method of target initiation, polymerase extension occurs in the presence of the priming substrate reagent, an excess of deoxynucleoside triphosphates, and an agent for polymerization, as shown in FIG. 5. The polymerization template method is particularly beneficial, because all of the necessary reagents, except for the substrate precursor, may be employed in the catalytic method for oligonucleotide generation which follows target initiation.

In the polymerization template target initiation scheme shown in FIG. 5, a single substrate precursor $SP_1$ is provided with a cutting attenuation modification. This single substrate precursor is designed to hybridize at or near a naturally occurring restriction site in the target sequence. In this way, catalytic primer extension through the naturally occurring restriction site in the target creates a complementary site in the substrate reagent which, but for the positioning of the cutting attenuation modification on the substrate precursor primer, would be a restriction enzyme recognition site. The duplex thus formed between the extended modified catalytic primer and the target can then be contacted with a cutting agent to selectively cleave the target, releasing an activated substrate reagent. Just as in target-primed ligation template initiation, it is possible to achieve isothermal denaturation of the portion of the target not responsible for priming by initial temperature selection for the reaction. This form of polymerization template target initiation is also target-primed, or in this case "target-activated", because cleavage of the target strand occurs at the same cutting site which is preferably used in the subsequent catalytic oligonucleotide production method.

Still other variations of target initiation will be apparent to those skilled in the art, based upon the teachings of the present invention. These other methods may include additional ligation template initiation schemes as well as polymerization template initiation schemes. It will be appreciated that "hybrid" methods employing both ligation template and polymerization template schemes may provide additional advantages.

Cascade

Figure 6:
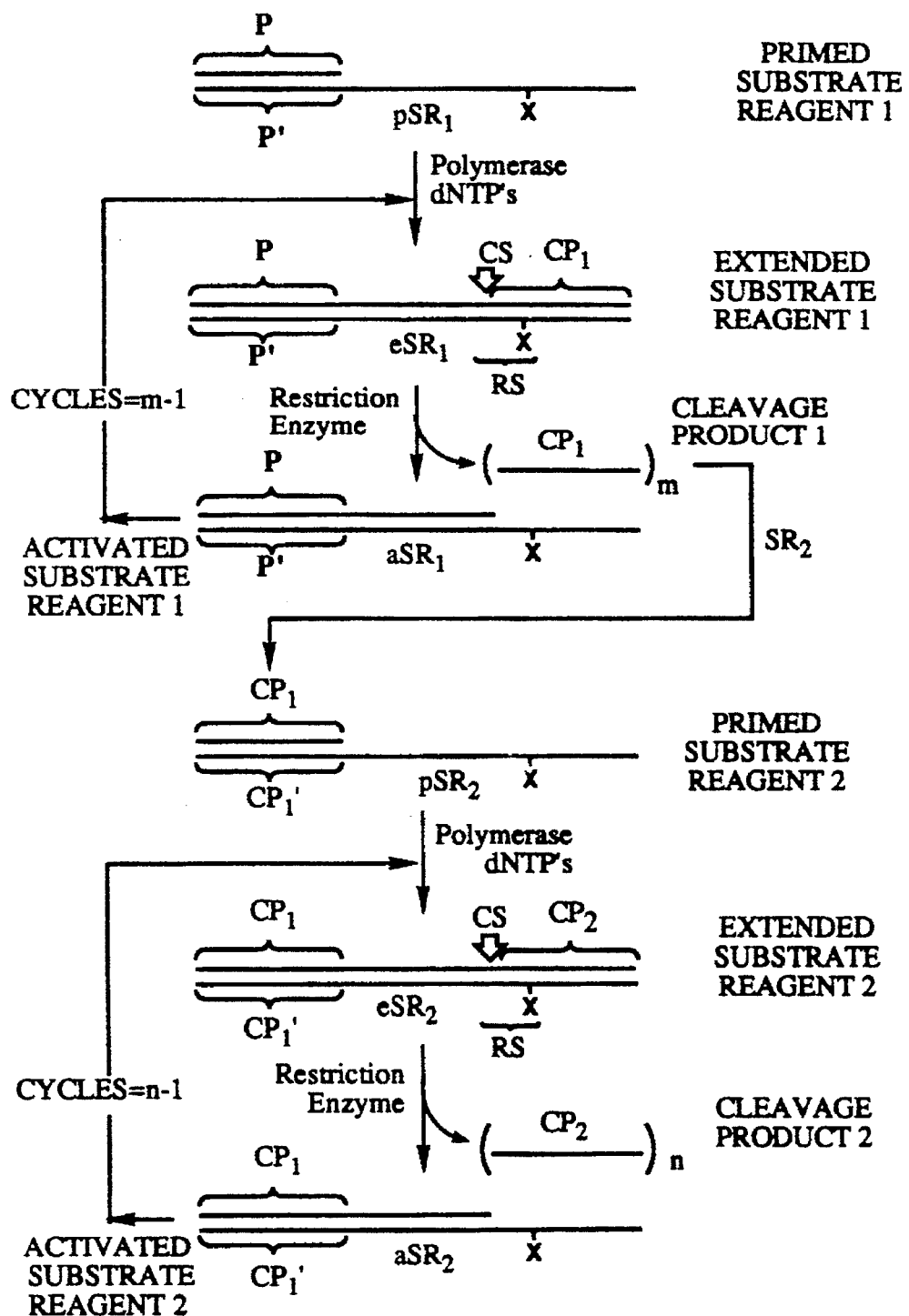
FIG. 6 is an illustration of a two level cascade using a series of two substrate reagents of the present invention.

The applicability of the catalytic oligonucleotide generation method of the present invention can be further broadened if a cascade of substrate reagents is used. Although a single substrate reagent is sufficient and preferred for traditional purposes of oligonucleotide synthesis, a series of substrate reagents can be employed as a cascade, such that the product from the first level of the cascade catalyzes the generation of product at the second level, and so forth, thereby dramatically increasing the output of final oligonucleotide product, as shown in FIG. 6. This cascade is of particular value in diagnostic applications where target is present in extremely low quantities. (A single substrate reagent may offer sufficient sensitivity in certain diagnostic situations where the amount of target in a test sample is relatively high.) In a typical diagnostic application, the target, although present in minute quantity, is able to initiate the cascade, which then rapidly generates an exponentially greater quantity of final oligonucleotide product which can be measured in a traditional type of detection system. The amount of final oligonucleotide product can then be correlated back to determine the amount of original starting target oligonucleotide.

In employing a cascade, the substrate reagents and corresponding cutting agent(s) are selected in much the same manner as for a one substrate reagent reaction. Importantly, the first substrate reagent in the series must be pre-primed or pre-activated. Where an amplification cascade is employed in a diagnostic setting, target initiation will be required to produce the first substrate reagent, thereby setting the cascade in motion. The composition of this first substrate reagent will therefore be dictated by the initiation scheme which has been selected. At all other levels of the amplification cascade, the substrate reagent is presented as a complete, but unprimed, presynthesized reagent. Each substrate reagent will typically be designed in the order of its appearance in the cascade, since the cleavage product from the first level must be complementary to the priming region of the second level substrate reagent, and so forth. It is preferred to use the same cutting agent and same cutting attenuation modification in the substrate reagent at all levels of the cascade in order to minimize the number of reagents required to run the reaction.

It has unexpectedly been found that, like the single substrate reagent reaction, the cascade can proceed isothermally. In other words, the cleavage product from one level of the cascade can be made to denature from its substrate reagent template and subsequently hybridize to the priming region of the next substrate reagent for a sufficient length of time to prime the in situ synthesis of oligonucleotide product at this new level of the cascade without a change in temperature. This is unexpected, because the $T_m$ for the oligonucleotide cleavage product bound to its complementary substrate reagent is substantially identical, to the $T_m$ for the same oligonucleotide product acting as catalytic primer by hybridizing to the priming region of the next substrate reagent in the cascade. (In fact, in the case where a tailing sequence is incorporated into cleavage product/catalytic primer, the $T_m$ for the priming reaction will be lower.)

It is believed that the oligonucleotide cleavage product hybridizes to the next level substrate reagent just long enough to allow for polymerase extension to produce a longer oligonucleotide product with a higher $T_m$. This produces the net effect of "locking" the oligonucleotide onto the new substrate reagent so that it can no longer hybridize to the complementary portion of the previous substrate reagent. The use of an intervening region is therefore particularly preferred in a cascade, because it provides for the generation of an activated substrate reagent with a higher $T_m$ than the primed substrate reagent, making the activated substrate reagent more stable than the primed substrate reagent.

It is imperative in a diagnostic setting that the substrate reagent(s) at higher levels of the cascade not be pre-primed, as generation of cleavage product at each level must be triggered only by the presence of target. In the first level of a diagnostic amplification cascade, generation of cleavage product is triggered by target initiation which provides the first substrate reagent. Cleavage of the extended substrate reagent not only generates catalytic primer for the next level of the cascade, but, as in the case of a single substrate reagent reaction, it also releases an activated substrate reagent to again act as a template for the in situ generation of another copy of extended substrate reagent at the current level. Once primed in the first instance by binding of a complementary catalytic primer, the substrate reagent at higher levels of the cascade need not be primed again in order to act as template for the formation of additional extended substrate reagent in subsequent cycles of in situ synthesis at the same level of the amplification cascade.

As each level beyond the first level of the cascade cycles, the amount of cleavage product generated at these higher levels grows exponentially as new primed substrate reagents are continually added to the partial duplex pool of recycled activated substrate reagents. This phenomenon is demonstrated in FIG. 6. As shown in this two level amplification cascade, the primed first substrate reagent $pSR_1$ acts as a template to create a first extended substrate reagent $eSR_1$. This extended substrate reagent is then contacted with a cutting agent, in this case a restriction enzyme, which cuts only the upper strand, as illustrated, at point CS. The reaction is preferably run at a temperature such that the cleavage product $CP_1$ isothermally denatures from the cleaved extended substrate reagent. Denaturation releases $CP_1$ to act as a catalytic primer in the second level of the cascade, also releasing the activated substrate reagent $aSR_1$ to be recycled in the first level of the cascade. Unlike higher levels, the amount of partial duplex in the first level of the cascade is "fixed", as all of the $pSR_1$ initially present (e.g., from target initiation) is ultimately converted to $aSR_1$. Product which is generated from the fixed amount of target-initiated partial duplex ($pSR_1$ or $aSR_1$, depending upon the particular initiation method) "accumulates" linearly at this first level. (There is no actual "accumulation" of $CP_1$, because virtually all of the $CP_1$ is consumed by the next level of the cascade.) This cycle of events will repeat itself m-1 times to produce m copies of $CP_1$.

The released $CP_1$ serves as catalytic primer for the in situ synthesis of a second extended substrate reagent ($eSR_2$) at the second level of the amplification cascade by priming $SR_2$. The $eSR_2$ is subsequently cleaved to release cleavage product $CP_2$ and the activated substrate reagent $aSR_2$. As described for the first level reaction, this second level will repeat itself n-1 times to form a total of n copies of $CP_2$ from each copy of $CP_1$. In the case of the two level cascade shown in FIG. 6, $CP_2$ will accumulate exponentially with respect to the starting target nucleic acid sequence, because the supply of $pSR_2$ and $aSR_2$ is continuously increasing as a result of the continued production of $CP_1$ from the first level of the cascade.

The yield of products in a particular cascade configuration follows a natural geometric progression that can be calculated where certain assumptions and definitions are imposed upon the system. These assumptions are necessitated by the fact that cleavage product of the present invention is actually generated by way of two related, but slightly different, mechanisms. In the first mechanism, the cycle of events generating the cleavage product is initiated by hybridization of a catalytic primer to a substrate reagent to form a primed substrate reagent (pSR). The cycle involving the second mechanism begins with an activated substrate reagent which has been generated from a previous first mechanism or second mechanism cycle. For purposes of defining the geometric progression, these two process are assumed to proceed at the same rate, with the production of one round of cleavage product from either of these processes being defined as one cycle. Following these assumptions, the fold amplification (X) in a 1, 2, and 3 level cascade after "n" cycles can then be calculated according to the following formula:

$$\text{One level: } X_{1,n} = n$$

$$\text{Two level: } X_{2,n} = \frac{(n)(n-1)}{2}$$

$$\text{Three level: } X_{3,n} = \frac{(n)(n-1)(n-2)}{6}$$

Similarly, the fold amplification "X" in a cascade of any level "c" after a given number of cycles "n" may then be calculated according to the following mathematical formula:

$$X_{c,n} = \frac{(n)(n-1)(n-2)\ldots(n-c-1)}{n!}$$

Figure 7:
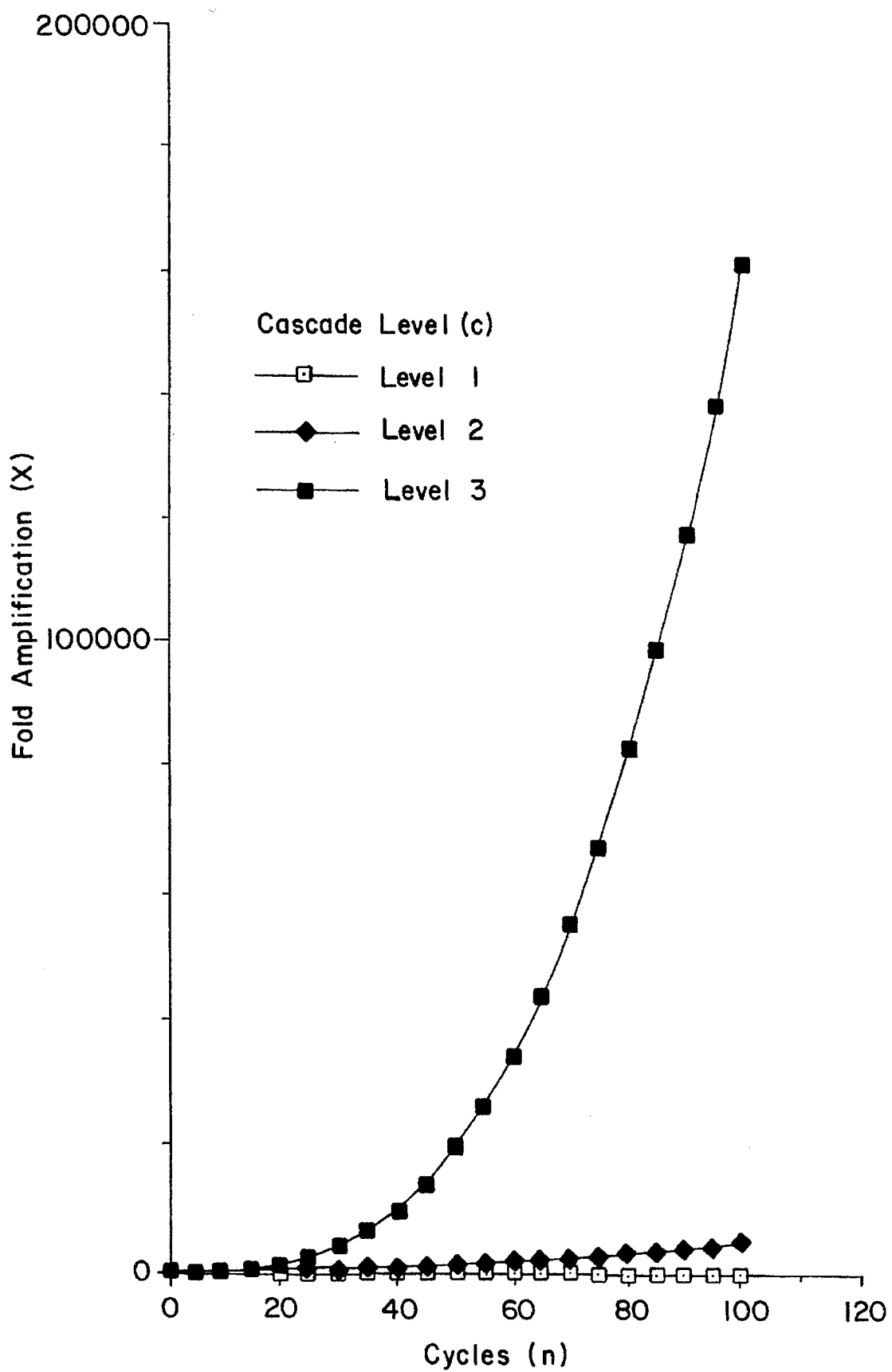
FIG. 7 graphically illustrates the fold amplification versus cycles for a one, two, and three level cascade.

Thus, after 100 cycling events, a one substrate reagent reaction will produce 100 copies of cleavage product $CP_1$ for each copy of primed substrate reagent $pSR_1$. A two level cascade will produce 4,950 copies of cleavage product $CP_2$ for each copy of first level primed substrate reagent $pSR_1$, while a three level cascade will produce 161,700 copies of cleavage product $CP_3$ for each copy of first level primed substrate reagent $pSR_1$. This geometric accumulation of products is shown graphically for a one, two, and three level cascade in FIG. 7. A three level cascade will produce over one million copies of third level cleavage product from each copy of primed first level substrate reagent after only 183 cycles.

The total number of cleavage products $N_{CP}$ produced in a reaction is the product of the number of molecules of first level primed substrate reagent $NpSR_1$, and the fold amplification $X_{c,n}$.

In diagnostic applications, the number of first level primed substrate reagent $pSR_1$ molecules is directly proportional to the number of target molecules $N_T$. In the "self-priming" embodiment of target initiation, one copy of $pSR_1$ is made from each target molecule each time the target initiation scheme is cycled. For the "target-priming" embodiment, a single copy of $pSR_1$ is made from each molecule of target.

The basis for the success of the amplification cascade rests on the priming of all higher level substrate reagent(s) by target-induced cleavage product from the previous level. It is, however, possible for some degree of non-target-induced priming of these unprimed substrate reagents to occur from one of two possible phenomena. Production of cleavage product by these processes is undesirable, because this "spurious" cleavage product introduces a background which can limit the sensitivity of the cascade diagnostic.

Figure 8:
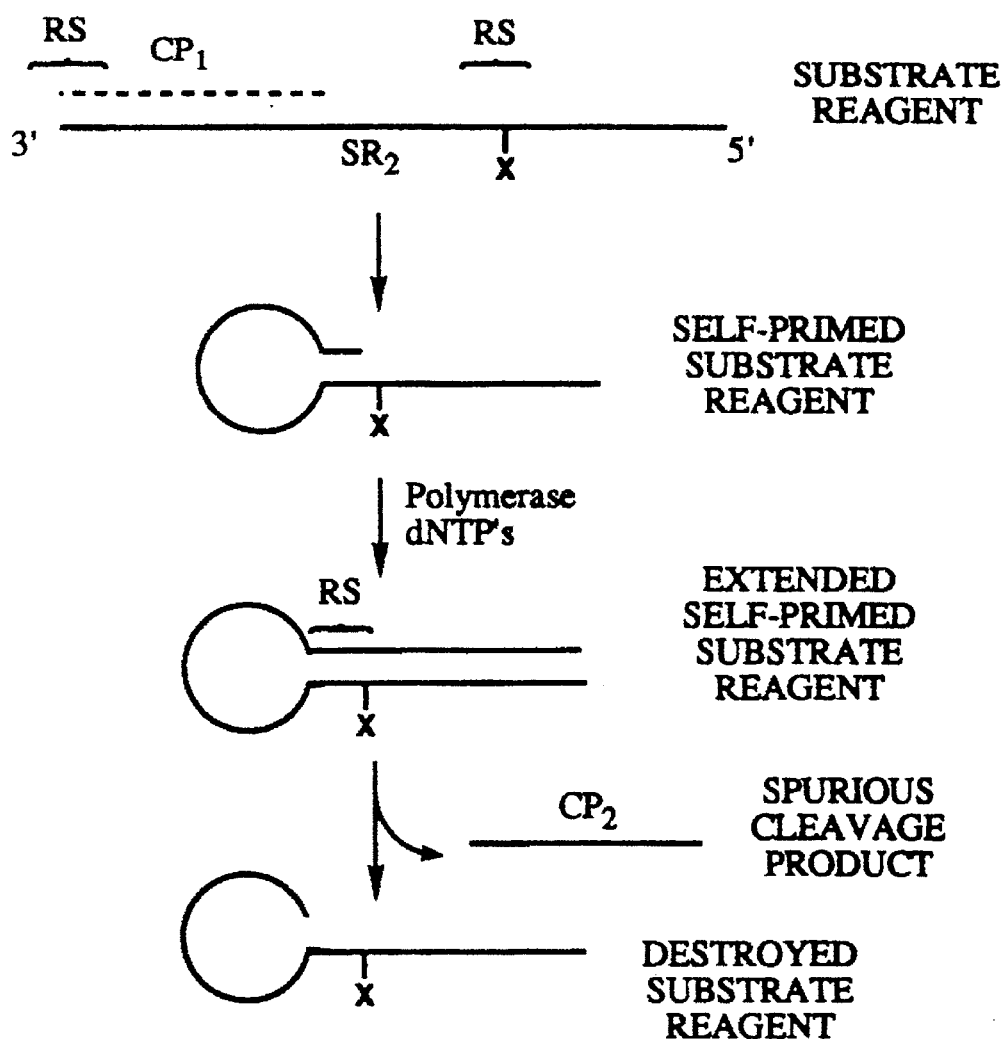
FIG. 8 demonstrates the undesired production of spurious cleavage product in a diagnostic setting from a self-primed substrate reagent which has folded back on itself.

The first of these non-target induced priming phenomena occurs where the substrate reagent at higher levels exhibits a tendency to fold back on itself in such a way that it becomes self-priming. The potential for this undesired type of self-priming is of particular concern in the majority of cascade formats employing restriction enzyme cutting agents, because most of these restriction enzymes normally generate 5'-overhangs. In this case, the cleavage product from the previous level substrate reagent will necessarily carry with it a significant portion of the restriction site. This creates certain design limitations from the fact that the priming end of the next higher level substrate reagent must be complementary to the previous level cleavage product, and will therefore also contain a significant portion of the restriction site sequence. As a result, spurious cleavage product can be generated from selective cleavage of the self-primed extended substrate reagent, as shown in FIG. 8.

Figure 9:
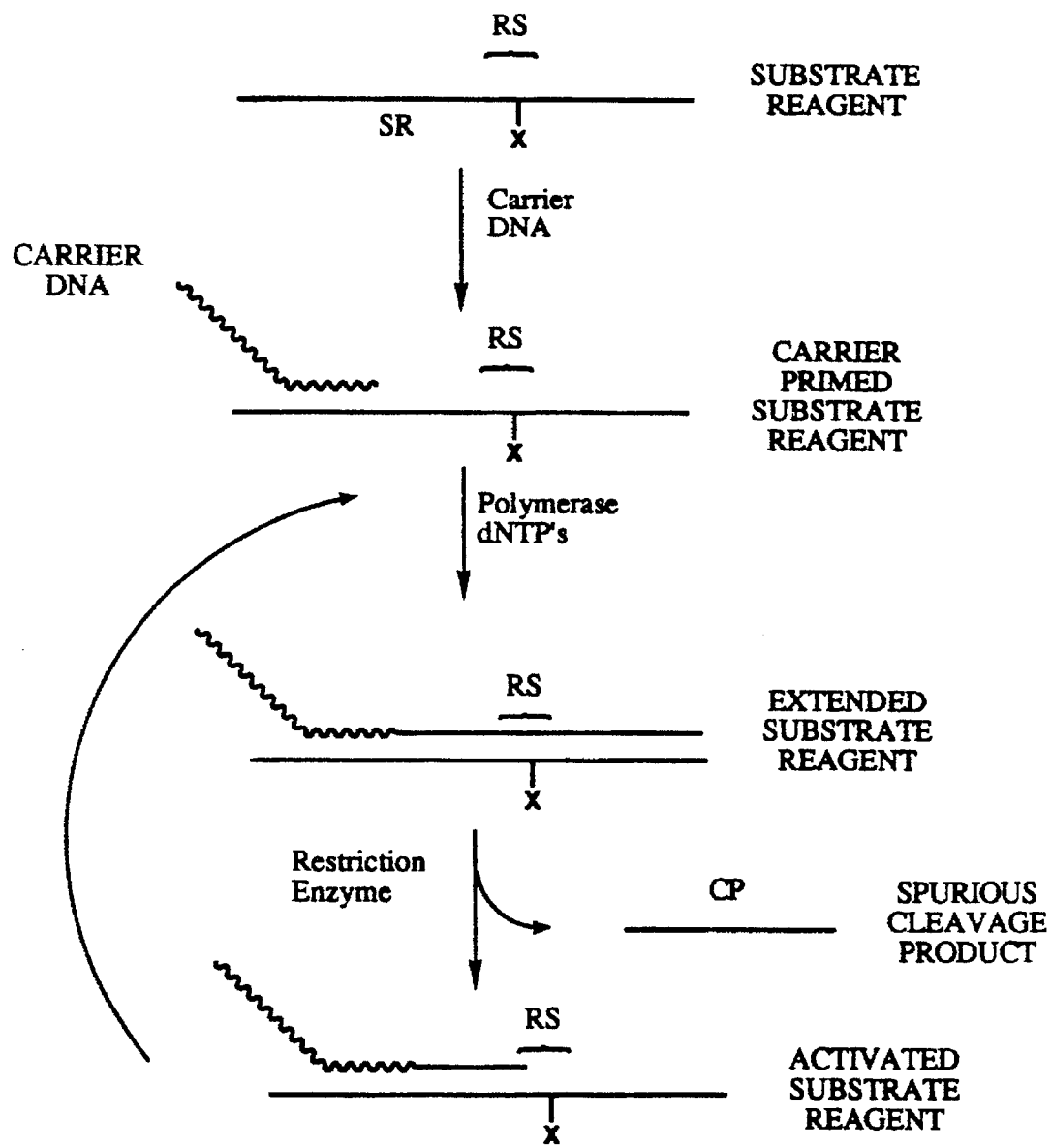
FIG. 9 demonstrates the undesired production of spurious cleavage product in a diagnostic setting from a substrate reagent that is nonspecifically primed with carrier DNA.

The second phenomenon involves nonspecific priming of the unprimed higher level substrate reagent(s) by the carrier DNA present in a test sample, as shown in FIG. 9. Carrier priming occurs where the 3'-end of a carrier DNA fragment partially hybridizes opposite the priming region and/or intervening region of the substrate reagent long enough to initiate polymerase extension. This typically leads to the generation of spurious cleavage product from the resulting extended substrate reagent. Where a sufficient number of carrier DNA bases remain hybridized to the substrate reagent following selective cleavage and partial denaturation, the substrate reagent/carrier partial duplex may be stabilized against denaturation at the assay temperature of the cascade, creating a spurious activated substrate reagent. This problem is particularly acute, because the spurious activated substrate reagent can now recycle to produce additional copies of spurious product.

Figure 10:
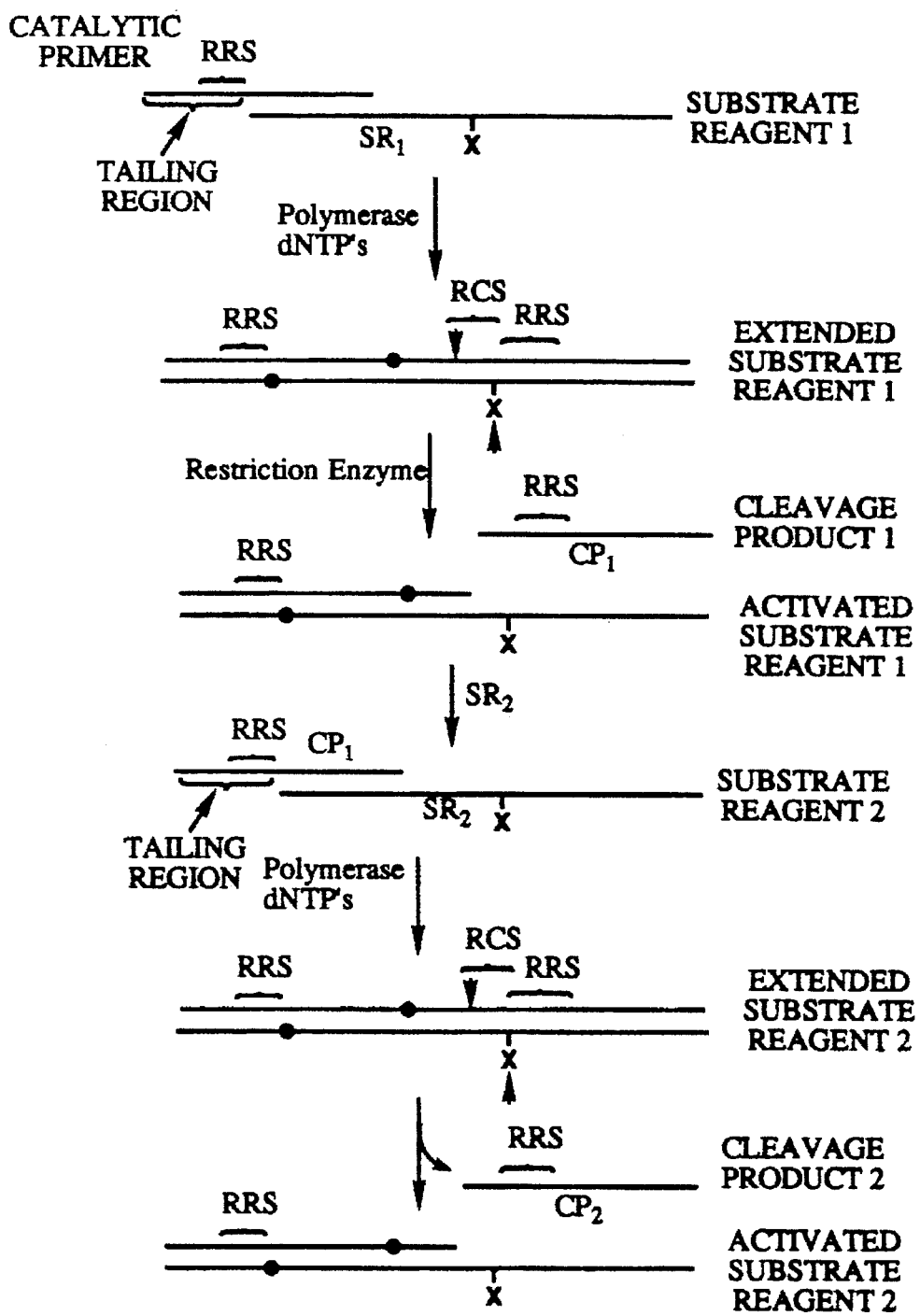
FIG. 10 demonstrates the production of cleavage product from a two level cascade using catalytic primers which contain a tailing sequence, where the tailing contains a remote recognition site.

The problem of non-target-induced priming of higher level substrate reagents can be significantly overcome either by adding an optional capping region on the substrate reagent, or by providing a tailing sequence on the catalytic primer. In the latter case, the priming region of each higher level substrate reagent in the amplification cascade will be of a shorter length than the cleavage product (containing the tailing sequence) from the previous level of the cascade.

Where a capping region is used, it is placed at the the 3'-end of the substrate reagent contiguous to the priming region, such that the 3'-end of the substrate reagent extends beyond the 5'-end of the catalytic primer. The function of the capping region is to prevent polymerase extension of the 3'-end of the substrate reagent in the event that the substrate reagent folds back on itself. This desired end result is preferably achieved by disrupting the 3'-end of the substrate reagent. For example, a dideoxynucleoside could be added to the 3'-end of the priming region.

Where the 5'-end of the catalytic primer extends beyond the 3'-end of the substrate reagent, the "tailing sequence" of the extended portion of the catalytic primer provides a template which can be filled in by the same polymerase and excess of dNTP's that are provided in the reaction mixture, as shown in FIG. 10. The use of a tailing sequence on the catalytic primer is particularly advantageous when it is used in combination with a remote cutting restriction enzyme to effect cleavage of the extended substrate reagent. As shown in the two level cascade in FIG. 10, the corresponding remote cutter recognition site is incorporated into the previous level cleavage product, but is not recognized by the remote cutting restriction enzyme at the next level until the remote site on the cleavage product/catalytic primer is made double-stranded by polymerase extension opposite the tailing sequence.

The tailing sequence on the catalytic primer can be as little as one nucleotide long, as long as it completes the necessary remote recognition site. Where a tailing sequence is incorporated into the catalytic primer, it is not necessary to also include a 3'-end capping region on the substrate reagent. Although self-priming and subsequent extension may still occur from folding back of the substrate reagent, this alone cannot create the remote recognition site required for selective cleavage by the cutting agent to generate the undesired spurious cleavage product. In this event, the only deleterious effect on the system will be the effective elimination of the self-primed substrate reagent from participation in the cascade. Similarly, carrier priming and subsequent extension fails to create the necessary remote recognition site for release of cleavage product, leading to the same result.

For diagnostic purposes, the final oligonucleotide cleavage product of a target-initiated amplification cascade is used as a measure of the presence of target in a test sample. This final "diagnostic" oligonucleotide product may be identical or complementary to a portion of the target sequence, or it may be wholly unrelated in sequence to the target. (A single substrate reagent reaction can also be designed to generate an oligonucleotide product which is different in sequence from the target or its complement.) Thus, a diagnostic system according to the present invention can be designed to be either a target amplification (where the final oligonucleotide product is identical or complementary to target) or a signal amplification (where an unrelated final oligonucleotide product is generated). It will generally be preferred to employ a signal amplification design, because the final oligonucleotide product in this type of design cannot participate as a carryover contaminant in future amplification runs. This provides a distinct advantage over target amplification systems such as PCR and LCR which are susceptible to these types of contamination problems.

The present invention also provides certain sensitivity and kinetic advantages over traditional diagnostic methods employing signal amplification. These earlier methods typically involve the attachment of multiple labels or catalytic moieties to a reporter probe in order to improve sensitivity. These reporter probes, which bind to the target nucleic acid sequence, are normally provided in large excess in order to achieve reasonable kinetics. It is, however, necessary to incorporate into these traditional probing techniques a method for separating excess unhybridized reporter probes from the target-bound probes prior to detecting signal from the target-bound reporter probe. Separation may be achieved through the pre-attachment of target to a solid support, either directly, or through a previously bound "capture" probe. The reporter probe becomes attached to the solid support through hybridization with the pre-attached target, leaving excess unhybridized probe available for removal through mechanical washing of the solid support. Signal measured from the solid support is indicative of the presence of target molecules.

Ideally, reporter probes become attached to the solid support(s) only through hybridization to target molecules. As a practical matter, however, sensitivity limiting background problems occur, because reporter probes can and do become attached to solid supports through other means of interaction with the support; i.e., through nonspecific binding and/or nonspecific hybridization. Signal from nonspecifically bound or nonspecifically hybridized reporter probes limits the achievable sensitivity in a given assay configuration. The sensitivity limit is reached when the signal from target-hybridized reporter probes approaches the level of signal produced through the nonspecifically bound or nonspecifically hybridized reporter probes. At lower levels of target, where these two types of signals approach the same intensity, it is impossible for an instrument or a human observer to distinguish between the two signals, and the presence or absence of target molecules becomes meaningless.

The method of the present invention takes advantage of a direct catalytic effect from a substrate reagent that is formed in response to the presence of target, rather than an indirect effect from catalytic groups attached to reporter probes. As a result, the present method avoids the types of background problems which result from nonspecific interactions caused by the large excess of these reporter probes which are introduced into the assay. Similarly, the previously mentioned CHA-based diagnostic assay uses target to directly catalyze the cleavage of an excess of labeled detection probe. In one embodiment, for example, the CHA method takes advantage of the catalytic effect of DNA on RNA substrates in the presence of RNAse H, previously reported by Berkawer et al, *J. Biol. Chem.*, 248(17), 5914–5921 (1973). In this particular CHA embodiment, the DNA target sequence acts directly as a catalytic co-factor for the RNAse H-induced cleavage of labeled RNA detection probes. Once the DNA target hybridizes with the RNA detection probe, the resulting DNA-RNA hybrid becomes a substrate for RNAse H, which selectively cuts the RNA strand of the duplex. Selective cleavage of the RNA strand lowers the effective $T_m$ of the duplex, allowing the RNA fragments melt off of the target sequence. The target may then be recycled to hybridize with another RNA detection probe.

The primary advantage of using target to catalyze signal generation lies in the potential to avoid sensitivity limiting background problems caused by nonspecific binding and nonspecific hybridization of catalyst introduced in large excess via the reporter probes. The CHA method, however, presents other potential sensitivity limiting features which are avoided by the method of the present invention. For example, the signal generated in a CHA reaction is measured by separating a large excess of the larger labeled detection probes from the resulting cleaved fragments which also carry the label. The sensitivity of the CHA method will therefore be limited to some degree by the efficiency of this separation step. Also, spurious, or non-target-catalyzed cleavage of CHA detection probes by a variety of means will introduce potential sensitivity limiting background into the assay, even if an efficient separation step is provided.

Importantly, the cascade method of the present invention relies on in situ synthesis, rather than cleavage of presynthesized probes, to achieve an amplified diagnostic result. The cascade initiation process itself involves the in situ synthesis of a first primed substrate reagent in the presence of target sequence using substrate precursors. Although these substrate precursor(s) of the present invention are provided in large excess with respect to the target, they cannot alone (i.e., without a template) produce a catalytic effect to generate signal or cleavage product. Similarly, because all of the catalytic elements in the cascade, as well as the final oligonucleotide product responsible for generating signal, are generated in situ through assembly from smaller elements (rather than through the destruction of larger elements as in CHA) the method of the present invention is not susceptible to the sensitivity limitations from spurious destruction of substrate molecules to which the CHA method is prone.

Both the catalytic primer(s) at higher levels in the cascade and the final oligonucleotide are indeed, by definition, "cleavage products". However, the extended substrate reagent precursors, required for generation of these cleavage products through selective cleavage, do not "pre-exist", but are, as previously noted, created in situ. In contrast, the signal-producing CHA cleavage products are present in large excess in the form of the cleavable detection probe precursors, enabling background signal products to be formed through the cleavage of a single covalent bond. The final oligonucleotide cleavage product in the method of the present invention must be assembled from monomeric deoxynucleoside triphosphates. This cannot occur spontaneously, and thus no background signal can result from spurious events.

Further, because the extended substrate reagent cleavage product precursors in the amplification cascade of the present invention are synthesized in situ, it is not necessary to separate the catalytic cleavage product precursors, or extended substrate reagents, by attachment to a solid support, as would be the case for a CHA type of cascade. Thus, the exponential cascade accumulation of signal-producing oligonucleotide cleavage product in the present invention can proceed in a kinetically unrestrained homogeneous environment Additionally, the unincorporated portion of the large excess of nucleoside triphosphates which is used to generate the signal-generating oligonucleotide cleavage product of the present invention need not be removed or separated in order to detect the presence of the resulting target-derived oligonucleotide product. Sensitivity does not suffer from the unnecessary incorporation of a separation step.

In some instances, it may be desired to use a cascade for purposes of synthesizing oligonucleotides. In this case the complementary portion of the last substrate reagent will be selected to be complementary to the desired oligonucleotide product. The remaining substrate reagents in the cascade will typically be designed in reverse order of their appearance in the cascade. In other respects, the cascade will proceed substantially as discussed for the amplification cascade used for diagnostic purposes.

The following examples are provided to aid in the understanding of the present invention, the true scope of which is set forth in the appended claims. It is understood that modifications can be made in the procedures set forth, without departing from the spirit of the invention.

EXAMPLE 1

Synthesis of Oliaonucleotide Reagents

The oligonucleotide reagents in the examples were synthesized using an Applied Biosystems model 380B synthesizer (Applied Biosystems, Inc., Foster City, Calif.) using cyanoethyl phosphoramidites and purified by polyacrylamide gel electrophoresis as disclosed in International Patent Application No. 89/02649, which is incorporated herein by reference.

Figure 15:
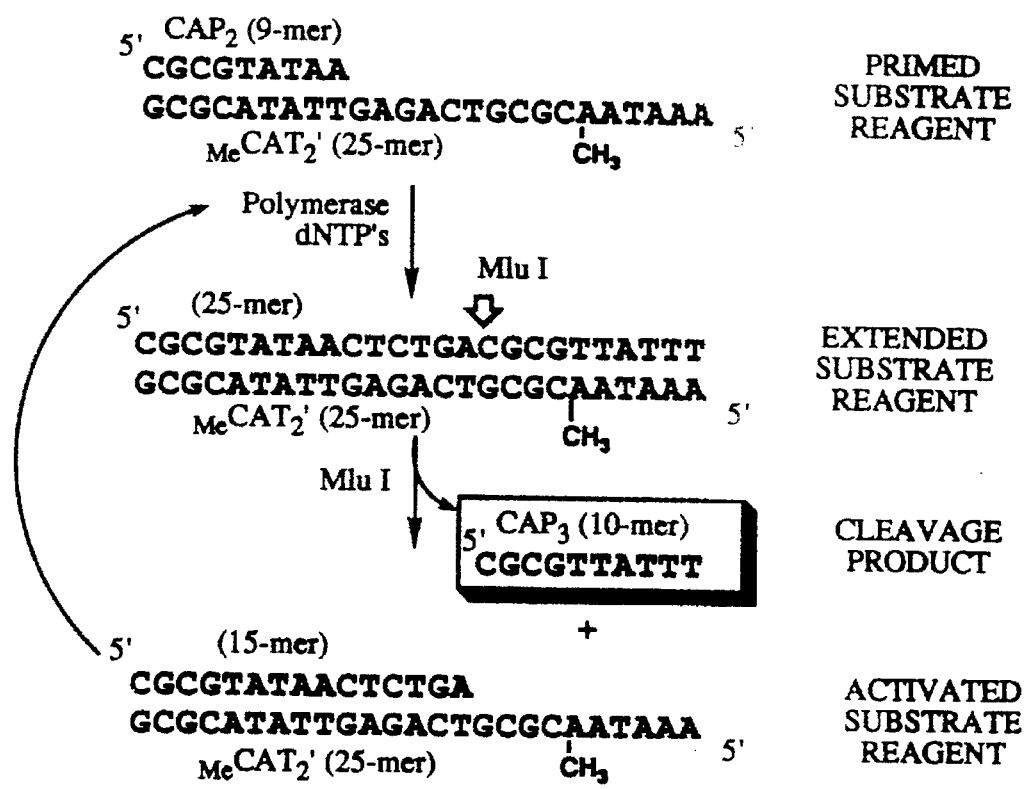
FIG. 15 illustrates the oligonucleotide sequences used to generate a cleavage product from a primed substrate reagent, as described in Example 4.

Unmodified oligonucleotide sequences $CAT_1$ and $CAT_1'$ (FIG. 11), $CAP_1$ (FIG. 13), and $CAP_2$ and $CAP_3$ (FIG. 15) were synthesized without modification. The preparation of the nucleotide analogs was as follows:

Phosphorothioate-modified oligonucleotide $_sCAT_1'$ (FIG. 8) was synthesized as described, with the exception that the phosphate between "C" and "A" as shown in FIG. 8 at position "X" was oxidized for 400 seconds with 5% sulfur in pyridine:carbon disulfide (1:2, v/v) instead of $O_2$/iodine. The product was deprotected and purified in the same manner as the unmodified oligonucleotide reagents.

Phosphorodithioate-modified oligonucleotide $_{ss}CAT_1'$ (FIG. 11) was synthesized in the same manner as the unmodified oligonucleotides, with the exception that the adenosine 5'- to the modified phosphate shown in FIG. 8 at position "X" was introduced as the 5'-dimethoxytrityl-N-benzoyldeoxyadenosine-3'-(N, N-dimethylamino)-(2,4-dichlorobenzylthiyl)-phoshine which was prepared according to the method of Caruthers et al., *J. Am. Chem. Soc.*, 111, 2321–2322 (1989). Following condensation with this modified phosphoramidite, the oligonucleotide was further oxidized with sulfur, as described above. The finished oligonucleotide was deprotected and removed from the resin using thiophenol followed by ammonia, as described in Caruthers et al, ibid. to produce the desired phosphorodithioate modified product.

Methylphosphonate-modified oligonucleotides $_{Me}CAT_1{'}$ (FIG. 11) and $_{Me}CAT_2{'}$ (FIG. 15) were synthesized in the same manner as the unmodified oligonucleotides, with the exception that the adenosine 5'- to the modified phosphate was introduced as the methyl phophonamidite, dA-Me Phosphonamidite (Glen research Corporation, Herndon, Va.). The final product was deprotected and removed from silica support by treating with 30% ammonium hydroxide:pyridine (1:1, v/v) for 4 days at 4° C., as described by Noble et al, *Nucl. Acids Res.*, 12(7), 3387–3404 (1984).

Methylthiophosphonate oligonucleotide $_{sMe}CAT_1{'}$ (FIG. 11) was prepared as the methylphosphonate oligonucleotides, with the exception that, after condensation with the modified adenosine, the phosphate was oxidized with sulfur as described above.

EXAMPLE 2

Screening of Potential Cutting Attenuation Modifications

Figure 11:
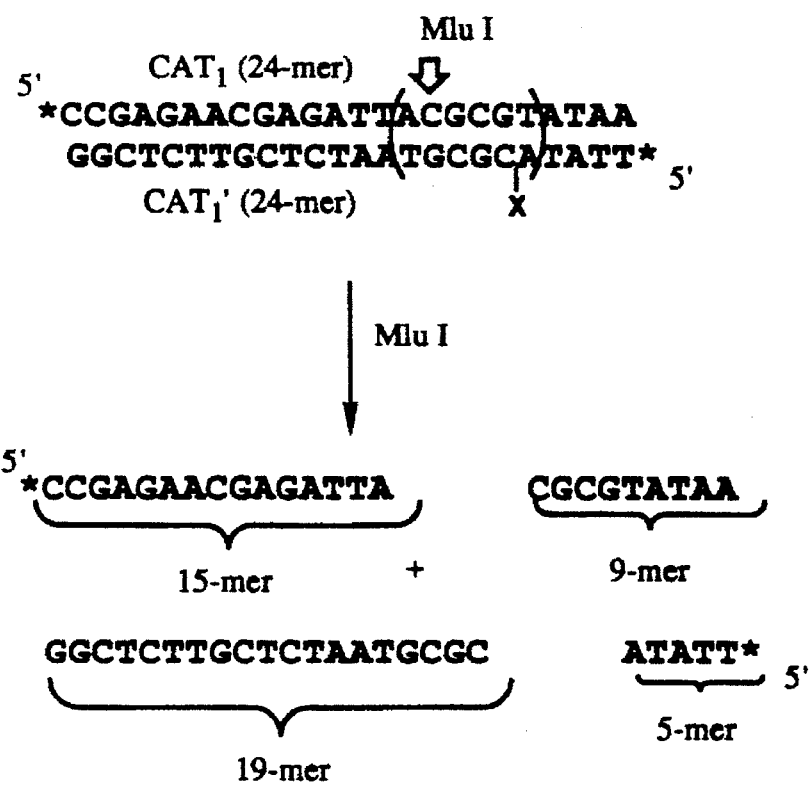
FIG. 11 illustrates the oligonucleotide sequences and phosphate modifications used in Example 2 to screen for potential cutting attenuation modifications.

This example demonstrates the first level of screening for a suitable cutting attenuation modification. The cutting attenuation modification should allow for cutting of the unmodified strand of a duplex while inhibiting cutting of the modified strand of a duplex. In order to screen for suitable modifications, several DNA duplexes containing a Mlu I recognition site (ACGCGT) with various phosphate modifications on one of the strands were prepared. A single phosphate modification was incorporated into the phosphate that participates in cutting by the restriction endonuclease. The sequences used in this evaluation are shown in FIG. 11. The Mlu I recognition site was located asymmetrically within the duplex such that resulting different fragment sizes could be used to determine the position of cutting. For example, cutting of the upper strand ($CAT_1$) yields a 15-mer oligonucleotide fragment and a 9-mer oligonucleotide fragment, while cutting of the lower strand ($CAT_1{'}$) yields a 5-mer oligonucleotide fragment and a 19-mer oligonucleotide fragment. Since only the 5'-ends of the duplex were initially labeled with $^{32}P$, only the resulting 15-mer oligonucleotide fragment from the upper strand and the 5-mer oligonucleotide fragment from the lower strand were expected to appear in autoradiography. Thus, an appropriate cutting attenuation modification located on only the lower strand, $CAT_1{'}$, was apparent by the appearance of a 15-mer oligonucleotide product, and little or no 5-mer oligonucleotide product upon exposure to the Mlu I cutting agent.

The following reagents were used:

A 10×reaction buffer was made to contain 100 μg/ml of bovine serum albumin, 500 mM NaCl, 100 mM Tris.HCl (pH 7.4), 100 mM MgCl2, and 100 mM 2-mercaptoethanol.

Mlu I restriction endonuclease was purchased from New England Biolabs (Beverly, Mass.) at a concentration of 8 units/μl.

Dye reagent was prepared to contain 11 mM EDTA, 83 mM boric acid, 100 mM Tris base, 10M urea, 0.02% bromophenol blue, and 0.02% xylene cyanole.

Oligonucleotides $CAT_1$, $CAT_1{'}$, $_sCAT_1{'}$, $_{ss}CAT_1{'}$, $_{Me}CAT_1{'}$, and $_{sMe}CAT_1{'}$ were phosphorylated with $\gamma^{32}P$-ATP (adenosine-5'-triphosphate) obtained from ICN Biomedicals, Inc. (Costa Mesa, Calif.), and T4 polynucleotide kinase (New England Biolabs) to a specific activity of approximately 7,000 Ci/mmole. These oligonucleotides were then used to adjust the specific activity of the respective unlabeled oligonucleotides to approximately 1,250 cpm/pmole.

Two independent sets of reactions were established to evaluate modifications of the phosphate as potential cutting attenuation modifications. Reaction Set A compared a phosphorothioate (Reaction 3) and a phosphorodithioate (Reaction 2) modification to the natural phosphate (Reaction 1). Reaction Set B compared a methylthiophosphonate (Reaction 6) and a methylphosphonate (Reaction 5) to the natural phosphate (Reaction 4). Each reaction was set up to contain a final volume of 25 μl of 1×reaction buffer and contained 20 pmole of $CAT_1$, and 16 units of Mlu I restriction enzyme. In addition to the above, the reactions also contained the following:

Reaction Set A

Figure 12A:
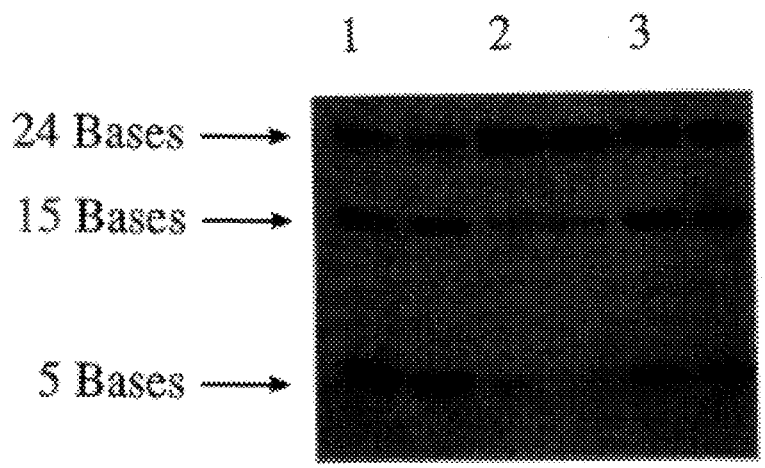
FIG. 12A and 12 are the autoradiograms of polyacrylamide gels used to separate the products generated in Example 2.

Reaction 1: 20 picomoles of $CAT_1{'}$
Reaction 2: 20 picomoles of $_{ss}CAT_1{'}$
Reaction 3: 20 picomoles of $_sCAT_1{'}$ Reaction Set B Reaction 4: 20 picomoles of $CAT_1{'}$
Reaction 5: 20 picomoles of $_{Me}CAT_1{'}$
Reaction 6: 20 picomoles of $_{sMe}CAT_1{'}$ The Mlu I restriction enzyme was added to the reactions after annealing of the oligonucleotides by heating to 90° C. for 2 minutes, followed by cooling at room temperature for 5 minutes. The cutting reactions were allowed to incubate for 1 hour at 37° C. The reactions were then quenched by adding 25 μl of dye reagent and heating to 90° C. for 2 minutes, followed by cooling to room temperature. The reaction products in the samples were analyzed by separation using 15% denaturing polyacrylamide gel electrophoresis (PAGE), followed by autoradiography. As shown in FIG. 12A, the natural phosphate duplex (Reaction 1, Lane 1) shows the expected cutting products, namely a 15-mer and a 5-mer oligonucleotide product, in roughly the same ratio.

It should be noted that in addition to these products, there is also some remaining 24-mer starting material that does not cut. This is a common occurrence, and is attributable to the fact that a certain population of synthetic oligonucleotides are not biologically active due to subtle modifications or incomplete deprotection, as earlier discussed. The phosphorodithioate modification (Reaction 2, Lane 2) shows both (15-mer and 5-mer) cleavage products, indicating that it is not an appropriate modification for this restriction site. It is interesting to note that this modification inhibits the overall cutting of both strands, probably by disrupting the substrate affinity for this enzyme. Similarly, the phosphorothioate modification (Reaction 3, Lane 3) was also ruled out as a cutting attenuation modification for use in combination with the Mlu I cutting agent, due to its apparent inability to impart cutting resistance.

Figure 12B:
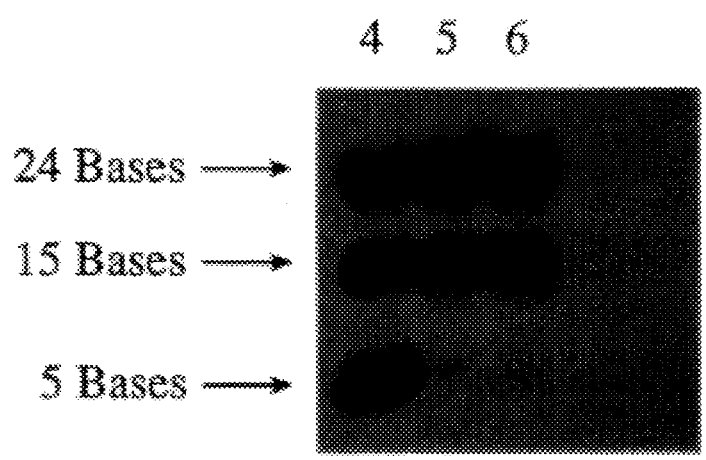

In contrast, as shown in FIG. 12B, both the methylphosphonate (Reaction 5, Lane 5) and the methylthiophosphonate (Reaction 6, Lane 6) provide very efficient cutting attenuation, as demonstrated by the presence of only a trace of the 5-mer cleavage product. Additionally, the duplexes still have good affinity for the enzyme as indicated by the formation of a comparable degree of 15-mer product, as compared to the unmodified duplex (Reaction 4, Lane 4). Thus, either of these cutting attenuation modifications meet the first requirement for cutting resistance, by their ability to attenuate cutting without interfering with substrate affinity and specificity.

EXAMPLE 3

Polymerase Extension Through Potential Cutting Attenuation Modifications

Figure 13:
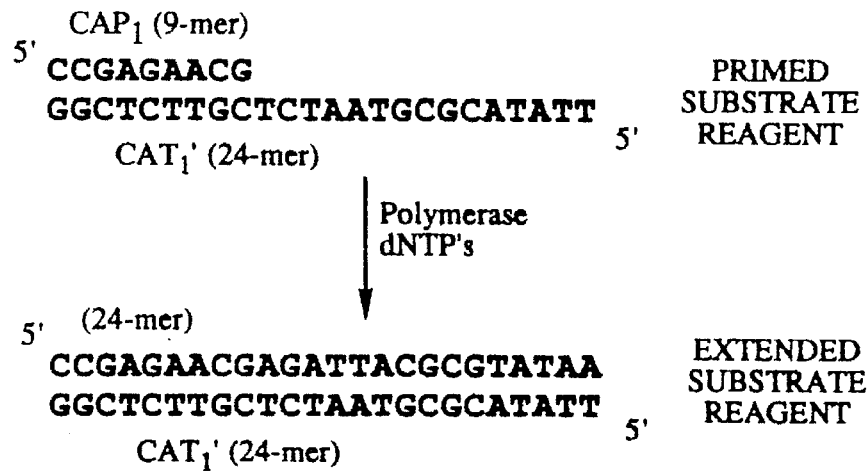
FIG. 13 illustrates the oligonucleotide sequences and cutting attenuation modifications used in Example 3 to evaluate potential interference of the polymerase reaction by various cutting attenuation modifications.
Figure 13:
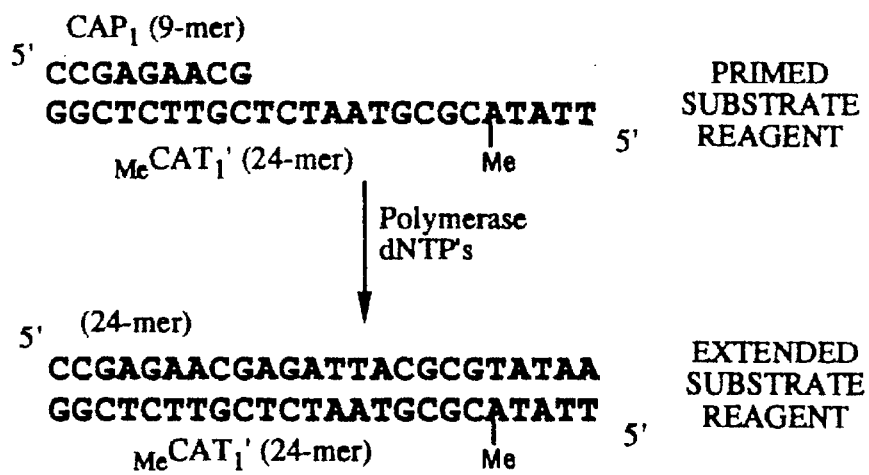
Figure 13:
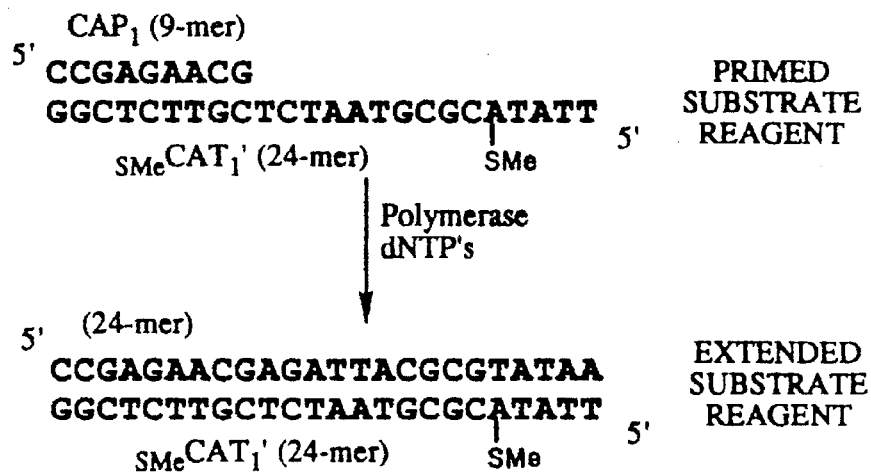

This example demonstrates a screening technique for a second requirement in selecting a cutting attenuation modification, namely the ability of a polymerase to extend through the modification. In order to address this requirement for the methylphosphonate and the methylthiophosphonate modifications, a 9-mer oligonucleotide sequence ($CAP_1$), complementary to the 3'-end of the $CAT_1'$ control sequence was synthesized for use as a catalytic primer in this extension example. As shown in FIG. 13, this catalytic primer is complementary to $CAT_1'$, $_{Me}CAT_1'$, and $^{SMe}CAT_1'$, and, in the presence of polymerase, and dNTP's, should be able to extend to form a 24-mer product, provided the cutting attenuation modification does not interfere with the polymerase activity. The products were labeled, for subsequent visualization, by incorporating $\alpha^{32}$P-dATP into the polymerase extension reactions.

The following reagents were used:

10×Extension Buffer was 100 mM Tris.HCl (pH 7.4, 100 mM $MgCl_2$, 100 mM 2-mercaptoethanol, and contained 100 µg/ml bovine serum albumin.

DNA Polymerase I Large Fragment (Klenow Fragment) was purchased at a concentration of 8 units/µl from New England Biolabs.

Deoxyadenosine-5'-triphosphate [alpha-$^{32}$P] ($\alpha^{32}$P-dATP) was purchased from ICN Biomedicals, Inc. at a specific activity of 3,000 Ci/mmole.

Deoxynucleoside-5'-triphosphates (dATP, dCTP, dGTP, and dTTP) were obtained as part of the Perkin Elmer Cetus (Norwalk, Conn.) GeneAmp™ DNA Amplification Reagent Kit.

Dye reagent was the same as used in Example 2.

The deoxyadenosine-5'-triphosphate used in the examples was adjusted to a specific activity of approximately 2,000 CPM/pmole by mixing the appropriate amount of $\alpha^{32}$P-dATP and dATP. In addition, the $^{32}$P-labeled $CAP_1$ from Example 2 was used as a 24-base marker in gel electrophoresis.

All reactions were run in a final volume of 10 µl of 1×Extension Buffer, and were 100 mM in each dNTP and contained 4 pmoles of $CAP_1$ and 1.0 units of Klenow Fragment Polymerase. In addition to the above, the reactions also contained the following:

Reaction 1: 2.0 picomoles of $CAT_1'$
Reaction 2: 2.0 picomoles of $_{Me}CAT_1'$
Reaction 3: 2.0 picomoles of $_{sMe}CAT_1'$ The Klenow Fragment polymerase was added to the reactions last, after annealing by heating to 90° C. for 2 minutes, followed by cooling to room temperature for 5 minutes. The extension reactions were allowed to run for 15 minutes at room temperature, and then quenched by the addition of 10 µl of dye reagent and heating to 90° C. for 2 minutes, followed by cooling again to room temperature. The products, along with a $^{32}$P-labeled 24-mer oligonucleotide which was used as a marker, were separated by running on 15% denaturing PAGE and visualized by autoradiography.

Figure 14:
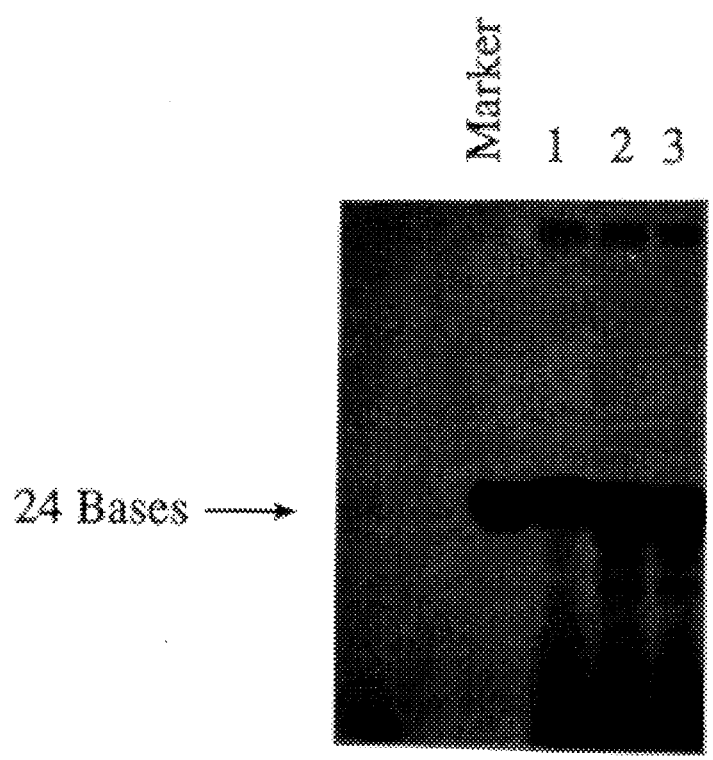
FIG. 14 shows the autoradiogram of polyacrylamide gels used to separate the products generated in Example 3.

As shown in FIG. 14, all three CAT sequences serve as templates to form the 24-mer extended substrate reagent. Reaction 1 (Lane 1) formed a clean 24-mer fragment, while the modified template sequences in Reaction 2 (Lane 2) and Reaction 3 (Lane 3) formed the 24-mer extended substrate reagent and some less than fully extended products. Thus, both of these phosphate modifications meet the second requirement for the cutting attenuation modification with the exception that, in addition to the fully extended product, they also formed some less than fully extended product. The methylphosphonate modification was selected for the cutting attenuation modification in subsequent examples, because it is somewhat more convenient to prepare the methylphosphonate than the methylthiophosphonate modified sequence.

EXAMPLE 4

Synthesis of an Oligonucleotide Product Using a Methylphosphonate-modified Substrate Reagent The final requirement for an acceptable cutting attenuation modification is that it operate satisfactorily with the cutting agent and the polymerizing agent simultaneously in the same reaction environment. In order to test whether the methylphosphonate cutting attenuation modification would perform satisfactorily under these conditions, substrate reagent ($_{Me}CAT_2'$) and catalytic primer ($CAP_2$), shown in FIG. 15, were both treated with Klenow polymerase and Mlu I simultaneously. If both the cutting process and the extension process work in the same reaction, one should observe an accumulation of a 10-mer oligonucleotide cleavage product $CAP_3$. Additionally, the catalytic primer $CAT_2$ was titrated down in concentration in this example to confirm that production of $CAP_3$ was indeed due to the presence of catalytic primer. Label was incorporated into the products for subsequent visualization by using the radioactive $\alpha^{32}$P-dATP as described in Example 3.

In order to quantitate the accumulation of $CAP_3$ cleavage product, the same reactions were run using polymerase alone, without the cutting agent. In this case, all primed substrate reagent will extend to form a single copy of extended substrate reagent. The number of cycles to produce the observed amount of cleavage product ($CAP_3$) where both reagents are present could then be estimated by comparison to this signal, representing a single copy.

The following reagents were used:

Reaction Buffer, Dye Reagent, and Mlu I restriction endonuclease were the same as in Example 2.

Oligonucleotides $CAP_3$ and $_{Me}CAT_2'$ were labeled with $\gamma^{32}$P-dATP and polynucleotide kinase to a specific activity of approximately 7,000 Ci/mmole for used as markers in identifying reaction products in gel electrophoresis.

Deoxynucleoside triphosphates and Klenow Fragment polymerase were the same as in Example 3.

All reactions were run in a final volume of 15 µl of 1×Reaction Buffer, and were 67 µM in each dNTP and contained 4 pmoles of $_{Me}CAT_2'$ and 1.0 unit of Klenow polymerase. In addition, the reactions also contained:

Reaction 1: 2.0 pmoles $CAP_2$
Reaction 2: 2.0 pmoles $CAP_2$+8.0 units Mlu I
Reaction 3: 0.2 pmoles $CAP_2$
Reaction 4: 0.2 pmoles $CAP_2$+8.0 units Mlu I Reaction 5: 0.02 pmoles CAP$_2$
Reaction 6: 0.02 pmoles CAP$_2$+8.0 units Mlu I
Reaction 7: 0.0 pmoles CAP$_2$
Reaction 8: 0.0 pmoles CAP$_2$+8.0 units Mlu I The Klenow polymerase and/or Mlu I restriction enzyme were added last to the reaction mixtures after annealing by heating to 90° C. for 2 minutes followed by cooling to room temperature for 5 minutes. The enzyme(s) were added to the reaction mixtures in a volume of 5 µl, bringing the total volume to 15 µl. The reactions were allowed to incubate at 45° C. for 3.5 hours and quenched by adding 15 µl of dye reagent and heating to 90° C. for 2 minutes followed by cooling at room temperature. The reactions, along with a $^{32}$P-labeled 10-mer and a $^{32}$P-labeled 25-mer oligonucleotide marker, were separated by 15% denaturing PAGE and the products were visualized by autoradiography.

Figure 16:
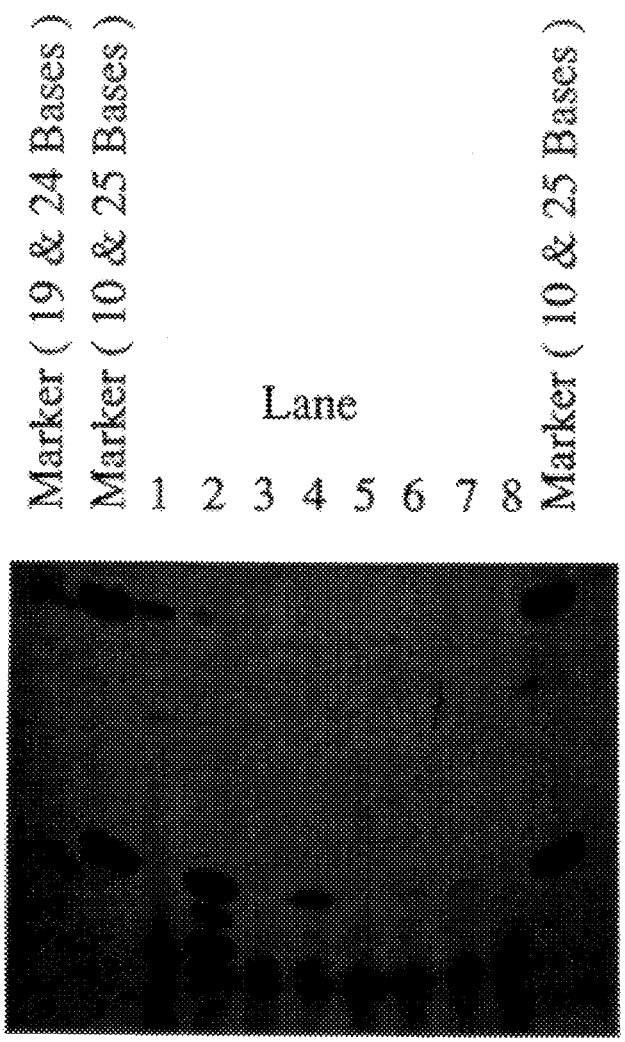
FIG. 16 shows the autoradiogram of polyacrylamide gels used to separate the products generated in Example 4.

The results shown in FIG. 16 suggest that multiple copies of the cleavage product (CAP$_3$) are indeed being formed. Reaction 1 (Lane 1), where no cutting agent was present, shows a 25-mer oligonucleotide product that represents a single copy of extended substrate reagent. In contrast, Reaction 2 (Lane 2) shows (in addition to the extended substrate reagent) an accumulation of the 10 base cleavage product CAP$_3$. It is interesting to note that, in addition to the expected 10-mer cleavage product, there is also an accumulation of shorter cleavage products, namely a 9-mer, 8-mer, and a 7-mer. These incomplete cleavage products most likely result from cleavage of the less than fully extended substrate reagents as observed in Example 3. Scanning laser densitometry using an UltroScan™ XL laser densitometer (Pharmacia LKB Biotech, Inc., Piscataway, N.J.) indicates that there is approximately 25 times more cleavage product than extended substrate reagent. This takes into account that the extended substrate reagent contains two radioactive adenosine moieties, and the cleavage products contain only one radioactive adenosine moiety. It is also apparent that the amount of cleavage product, as shown in Lanes 2, 4, 6, and 8 (Reactions 2, 4, 6, and 8, respectively) is formed in proportion to the amount of CAP$_2$ catalytic primer. As predicted, Reaction 8 shown that no 10-mer cleavage product CAP$_3$ is formed by substrate reagent in the absence of CAP$_2$ catalytic primer.

EXAMPLE 5

Cascade Production of Oligonucleotides

Figure 17:
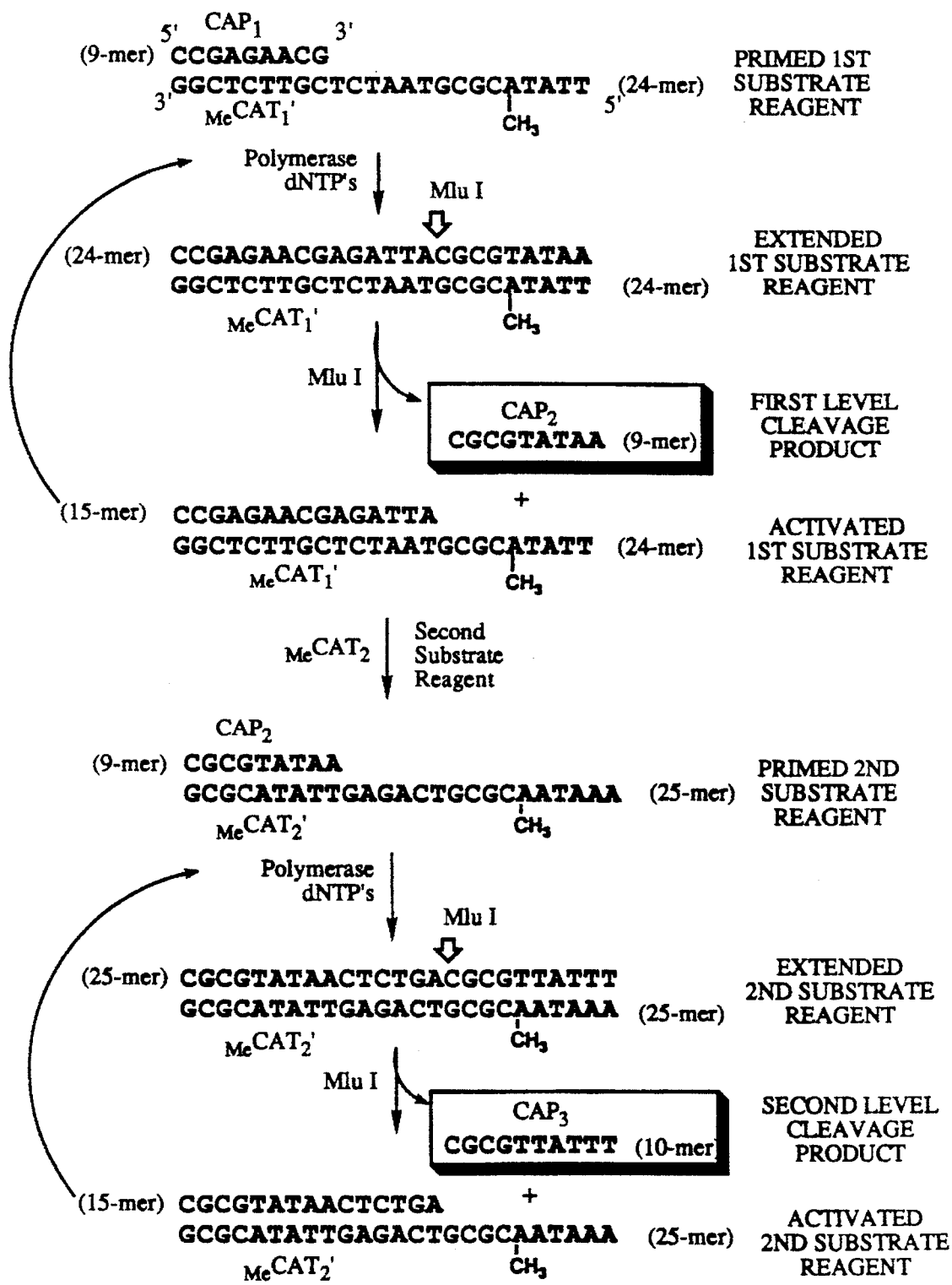
FIG. 17 illustrates the oligonucleotide sequences used to demonstrate cascade production of cleavage product, as described in Example 4.

The following example demonstrates the use of a two level cascade to produce an oligonucleotide cleavage product according to the scheme shown in FIG. 17. In this example, the first level of the two level cascade was allowed to cycle either by itself or in the presence of the second level substrate reagent. In addition, the first level substrate reagent was titrated down in concentration to confirm that any cleavage products were produced in response to its presence. As shown in FIG. 17, the two level cascade scheme used in this example was designed to produce a 9-mer first level cleavage product (CAP$_2$) and a 10-mer second level cleavage product (CAP$_3$). The size difference between the two cleavage products enabled the consequent differences in mobility of the products to be used as a 5 means for differentiation using denaturing PAGE separation. All products were labeled in situ through incorporation of $^{32}$P-labeled dATP, as in Example 3 and Example 4.

The following reagents were used:

Oligonucleotides CAP$_2$, CAP$_3$, $_{Me}$CAP$_2$, and $_{Me}$CAP$_1$' were phosphorylated on their 5'-ends using $\gamma^{32}$P-dATP (ICN Biomedicals, Costa Mesa, Calif.) and T4 polynucleotide kinase (New England Biolabs, Inc.) at a specific activity of approximately 7,000 Ci/mmole. These oligonucleotides were used as markers to characterize the resulting products which were analyzed by PAGE and autoradiography.

All other reagents were as described in Example 4.

All reactions were run in a final volume of 15 µl of 1×reaction buffer containing 4 pmoles of catalytic primer CAP$_1$, 1.0 unit of Klenow polymerase, and 8.0 units of Mlu I and were 66.7 µM in each dNTP (the dATP was adjusted to a specific activity of approximately 2,000 CPM/pmole). In addition to the above, the reactions also contained the following:

|  | $_{Me}$CAT$_1$' | $_{Me}$CAT$_2$' |
| --- | --- | --- |
| Reaction 1: | 250 fmoles | 4.0 pmoles |
| Reaction 2: | 25 fmoles | 4.0 pmoles |
| Reaction 3: | 2.5 fmoles | 4.0 pmoles |
| Reaction 4: | 0.0 fmoles | 4.0 pmoles |
| Reaction 5: | 250 fmoles | 0.0 pmoles |
| Reaction 6: | 25 fmoles | 0.0 pmoles |
| Reaction 7: | 2.5 fmoles | 0.0 pmoles |
| Reaction 8: | 0.0 fmoles | 0.0 pmoles |

The enzymes were added last to the reactions after annealing by heating to 90° C. for 2 minutes followed by cooling to room temperature for 5 minutes. Following addition of the enzyme, the reactions mixtures were incubated at 45° C. for 2 hours and 40 minutes. After incubation with the enzyme, the reactions were quenched by the addition of 15 µl of dye reagent and heated to 90° C. for 2 minutes, and then allowed to cool to room temperature. The resulting oligonucleotide products were analyzed, using standard techniques, by running the reaction mixtures and markers on 15% denaturing PAGE, followed by visualization on autoradiography.

Figure 18:
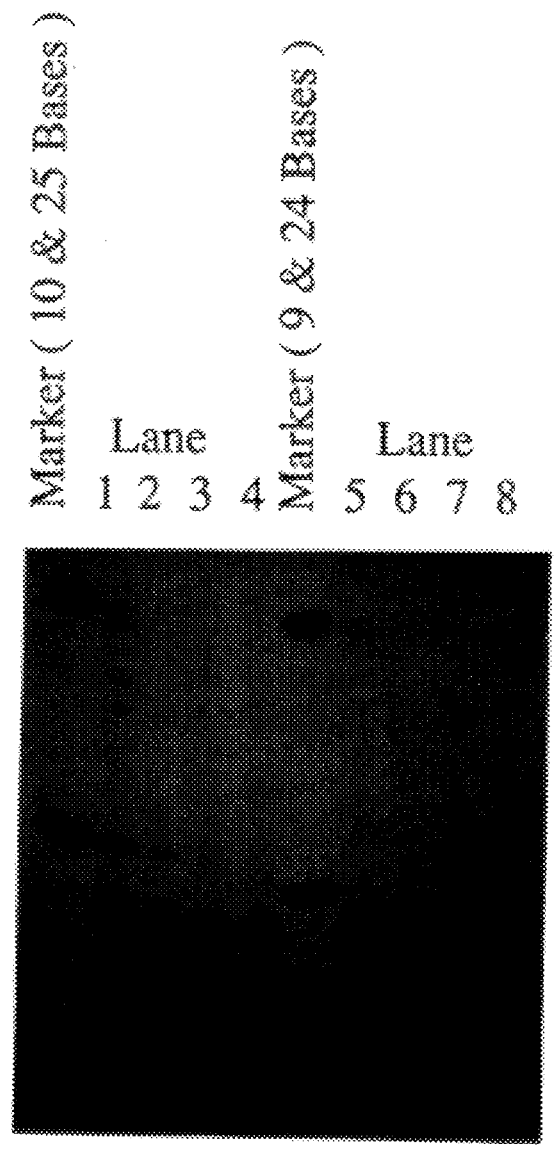
FIG. 18 shows the autoradiogram of polyacrylamide gels used to separate the products generated in Example 5.

As shown in FIG. 18, the desired 10-mer oligonucleotide cleavage product CAP$_3$ from the cascade was formed in Reactions 1, 2, and 3 (Lanes 1, 2, and 3, respectively), as determined by its similar mobility with respect to the 10-mer oligonucleotide marker (Lane M). Reaction 4 (Lane 4), which contains no first substrate reagent, showed no signs of cleavage product CAP$_3$, even upon prolonged radiography. This confirms that the desired cascade cleavage product CAP$_3$ in Reactions 1, 2, and 3 was produced specifically in response to the cascade. The cleavage product CAP$_2$ was also produced in a quantity proportional to the amount of starting substrate reagent $_{Me}$CAT$_1$'.

Further confirmation that the desired 10-mer cleavage product was indeed an end product of the cascade was obtained by analyzing the data for the Reactions run in the absence of the second level substrate reagent $_{Me}$CAT$_2$' (Reactions 5–8). Reaction 5 (Lane 5) shows that no 10-mer oligonucleotide product was formed in the absence of the second substrate reagent. The expected first level cleavage product was formed at a low level with the primary cleavage products from the first level of the cascade being the 8-, 7-, and 6-mer oligonucleotide products, which were apparently generated as the product of incomplete extension of the first level primed substrate reagent.

These "incomplete" first level cleavage products also appear in the corresponding two level cascade (Reaction 1, Lane 1) to approximately the same degree that they appear in the one substrate reagent reaction. This could be due to the fact that these "incomplete" cleavage products are not long enough to initiate priming of polymerase extension of the second level substrate reagent. It is also possible that if one were to design the system to generate longer cleavage products (e.g., a 12-mer oligonucleotide product), the "incomplete" cleavage products from this reaction (e.g., 11-, 10-, and 9-mer oligonucleotide products) would be capable of priming the next level of the cascade, thereby improving efficiency and, consequently, the yield of the desired end product.

In the present example, if one were to assume that only the full length 9-mer cleavage product from the first level of the cascade is capable of priming the second level substrate reagent, there is an approximate 100-fold benefit in sensitivity achievable by using the second level of the cascade. This calculation is based on the fact that the 9-mer oligonucleotide cleavage product formed in response to 250 femtomoles of $_{Me}CAT_1'$ in the one substrate reagent reaction (Reaction 5, Lane 5) is being formed at approximately the same level as the 10-mer oligonucleotide cleavage product formed in response to only 2.5 femtomoles of $_{Me}CAT_1'$ in the two level cascade (Reaction 3, Lane 3).

EXAMPLE 6

Figure 19:
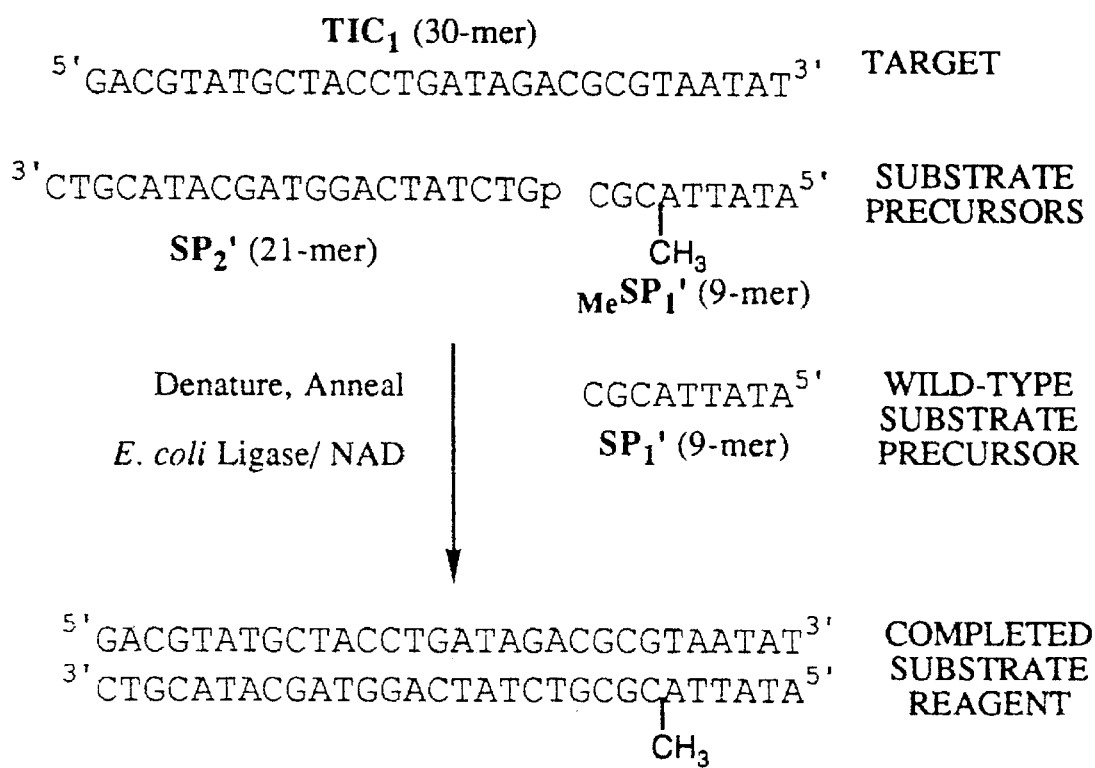
FIG. 19 illustrates the oligonucleotide sequences used to generate a completed substrate reagent from two substrate precursors in the presence of ligase, using target as a template, as described in Example 6.

Target-Dependent Synthesis of Substrate Reagent Using Substrate Precursors and Ligase This example demonstrates the synthesis of a completed substrate reagent from two substrate precursors in the presence of a target sequence, as illustrated in FIG. 4. The target sequence in this example serves as a template to bring the two precursor sequences (one of which contains a CAM) into contiguous proximity so that they can be covalently joined by the enzyme E. coli ligase. The oligonucleotide sequences used in this example are shown in FIG. 19.

The presence of the CAM near the ligation junction of oligonucleotide $_{Me}SP_1'$ was seen as a potential source of interference with the action of ligase in covalently joining $_{Me}SP_1'$ to $SP_2'$ in this type of target-initiated synthesis of substrate reagent. It was therefore decided to simultaneously evaluate a control system (employing wild type oligonucleotide $SP_1'$; i.e., not containing the CAM) in order to evaluate the influence of this particular CAM modification on the required ligation event. However, it should be noted that, while the ligation of $SP_1'$ to $SP_2'$ serves as an effective gauge of ligation efficiency, the resulting product is not an effective substrate reagent because it does not contain the necessary CAM.

Oligonucleotides $TIC_1$ (Target Sequence), $SP_1'$ (Control Substrate Precursor 1'), and $SP_2'$ (Substrate Precursor 2') were synthesized and purified as unmodified oligonucleotides, as described in Example 1.

Methylphosphonate-modified oligonucleotide $_{Me}SP_1'$ (Substrate Precursor 1') was synthesized and purified, as described in Example 1. The single methylphosphonate linkage, 3' to the adenosine, as shown in FIG. 19, was introduced to serve as a cutting attenuation modification (CAM) for Mlu I restriction endonuclease.

Adenosine 5'-triphosphate (ATP), used to phosphorylate oligonucleotide $SP_2'$, was purchased from Sigma Chemical Company (St. Louis, Mo.).

Radioactive $\gamma^{32}$P-ATP, at a specific activity of approximately 7,000 Ci/mmole, was purchased from ICN Biomedicals, Inc.

$T_4$ polynucleotide kinase, at a concentration of 10 units/µl, was purchased from New England Biolabs, Inc.

The enzyme E. coli ligase, at a concentration of 7 units/µl, was purchased from Boehringer Mannheim Corporation (Indianapolis, Ind.).

Nicotinamide adenine dinucleotide (NAD) was purchased from Sigma Chemical Company.

Oligonucleotides $TIC_1$, $SP_1'$, and $_{Me}SP_1'$ were phosphorylated on their 5'-ends to a specific activity of approximately 7,000 Ci/mmole using $\gamma^{32}$P-ATP and $T_4$ polynucleotide kinase. Excess ATP was separated from the labeled oligonucleotides by passing each reaction mixture over a Sephadex® G 50/50 column. Labeled $TIC_1'$ was used as a gel marker, while labeled oligonucleotides $SP_1'$ and $_{Me}SP_1'$ were used to incorporate labels into reaction products for visualization following gel electrophoresis.

Oligonucleotide $SP_2'$ was phosphorylated using $T_4$ polynucleotide kinase and $\gamma^{32}$P-ATP (diluted with ATP to a specific activity of approximately 1.0 Ci/mmole). The radioactive label was incorporated at a low specific activity as a means of following the phosphorylation efficiency. Excess ATP was separated from the labeled oligonucleotide by passing the reaction mixture over a Sephadex® G 50/50 column using triethylammonium bicarbonate as an eluant. Fractions containing the oligonucleotide were combined and then evaporated and resuspended in TE (Tris.HCl/EDTA). Scintillation counting showed that this oligonucleotide was phosphorylated quantitatively.

All ligation reactions (20 µl final volume) were run in 50 mM Tris (pH 7.6), 6.6 mM $MgCl_2$, 6.6 mM DTT, and 66 µM NAD, and additionally contained 0.5 mg/ml of BSA and 0.46 units of E. coli ligase. The reactions also contained the following:

| Reaction | $SP_1'$* (pmoles) | $_{Me}SP_1'$* (pmoles) | $TIC_1$ (pmoles) | $SP_2'$ (pmoles) |
|---|---|---|---|---|
| 1 | 0.0 | 4.8 | 0.0 | 5.0 |
| 2 | 0.0 | 4.8 | 0.0 | 5.0 |
| 3 | 0.0 | 4.8 | 2.0 | 5.0 |
| 4 | 0.0 | 4.8 | 2.0 | 5.0 |
| 5 | 0.0 | 4.8 | 0.0 | 0.0 |
| 6 | 0.0 | 4.8 | 0.0 | 0.0 |
| 7 | 4.8 | 0.0 | 0.0 | 5.0 |
| 8 | 4.8 | 0.0 | 0.0 | 5.0 |
| 9 | 4.8 | 0.0 | 2.0 | 5.0 |
| 10 | 4.8 | 0.0 | 2.0 | 5.0 |
| 11 | 4.8 | 0.0 | 0.0 | 0.0 |
| 12 | 4.8 | 0.0 | 0.0 | 0.0 |

*Specific activity of $SP_1'$ and $_{Me}SP_1'$ = 7,000 Ci/mmole

The reaction mixtures were heated to 90° C. for 2 minutes, and then cooled to room temperature to effect annealing of the substrate precursors to the target sequence. (The ligase was added to each reaction mixture after the annealing step, resulting in a final volume of 20 µl) After 1 hour at room temperature, 20 µl of dye reagent was added to each reaction, and the reaction tubes were then heated to 90° C. for 2 minutes to inactivate the enzyme. The reaction products were then analyzed by running the samples on denaturing 15% PAGE, followed by visualization using a PhosphorImager™ data collection device programmed with ImageQuant™ software (instrument and software from Molecular Dynamics, Sunnyvale, Calif.). The PhosphorImager™ device replaces the traditional use of photographic film to create a record of the separation data on the gel (i.e., autoradiography). The ImageQuant™ software, in combination with the PhosphorImager™ device, provides both: (1) qunatitative data, otherwise achieved through the use of densitometry; and, (2) a graphic "printout" representative of the image achieved in a traditional autoradiogram.

Figure 20:
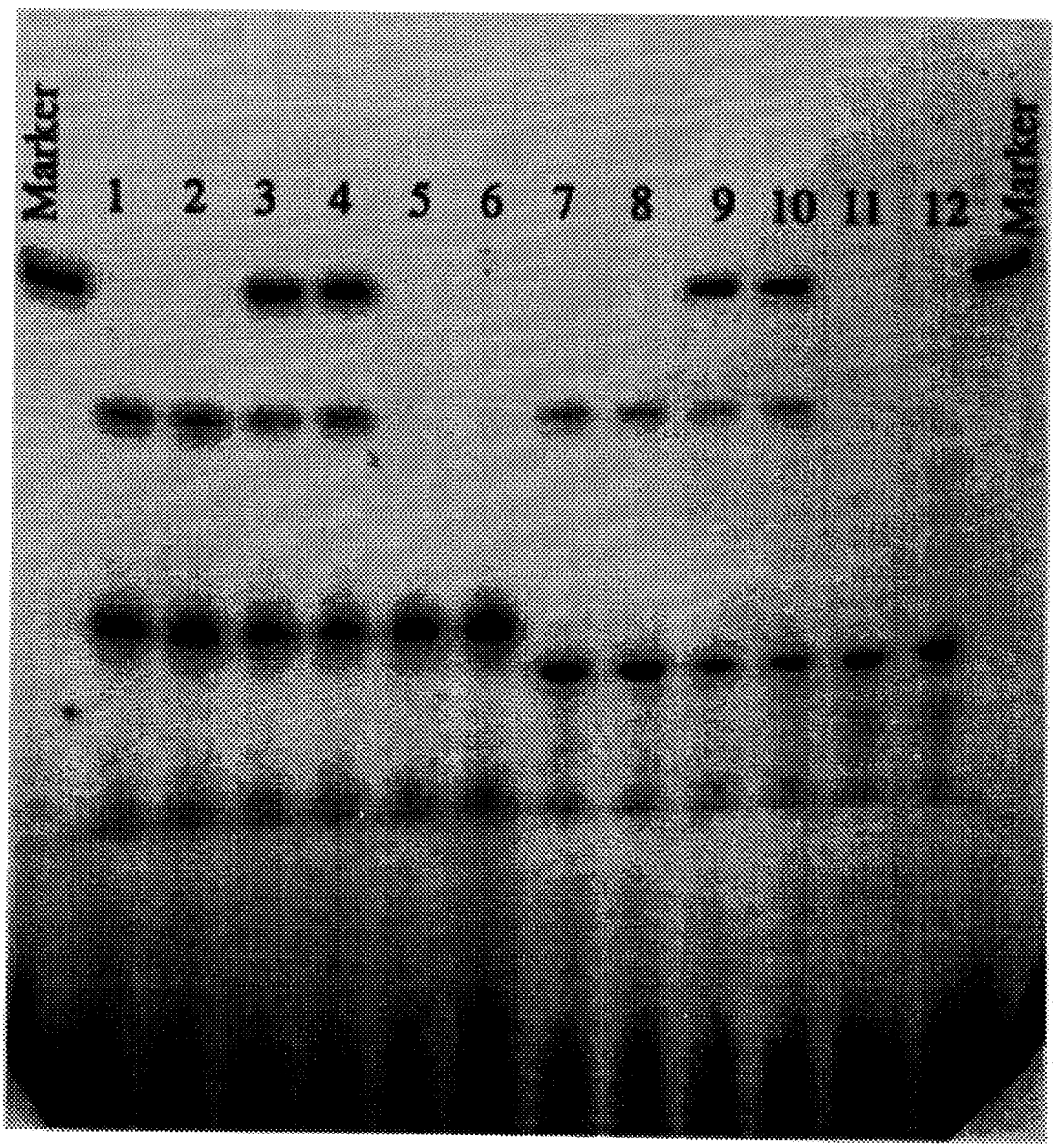
FIG. 20 is the PhosphorImager™ graphic printout of the polyacrylamide gel used to separate the products generated in Example 6.

A printout of the data from the PhosphorImager™ is shown in FIG. 20. Lanes 1–12 correspond to Reactions 1-12, respectively. Radioactive $TIC_1$ (30-mer) was loaded on either side of the gel for use as a marker. As shown in Lanes 3 and 4, the expected ligation product (30-mer) was formed from substrate precursors $SP_2'$ and $_{Me}SP_1'$ in the presence of target sequence $TIC_1$. In the case where both substrate precursors were wild type oligonucleotides ($SP_2'$ and $SP_1'$, Lanes 9 and 10, respectively) the 30-mer product formed in approximately the same yield. This suggests that the CAM-containing oligonucleotide $_{Me}SP_1'$ serves as an effective substrate for *E. coli* ligase despite the presence of the methylphosphonate internucleotide linkage in close proximity to the ligating junction. No 30-mer ligation product was formed in control reactions where either: (1) the target was absent (Lanes 1, 2, 7, and 8); or, (2) the target and substrate precursor $SP_2'$ was absent (Lanes 5, 6, 11, and 12). This confirms that the product is formed as a direct result of the presence of target in the reaction mixtures.

EXAMPLE 7

Figure 21:
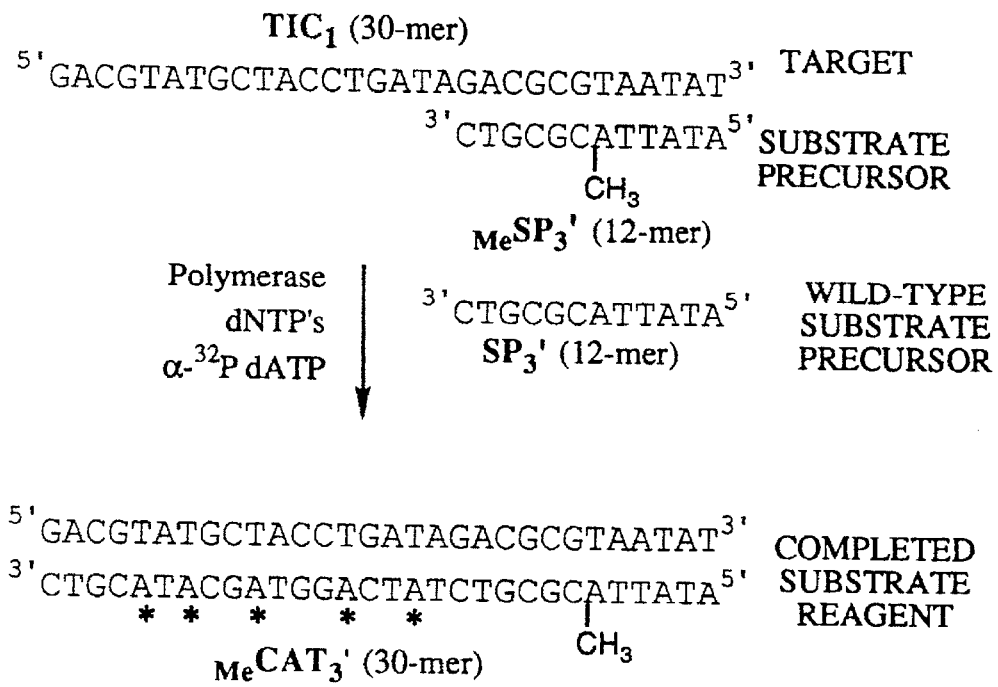
FIG. 21 illustrates the oligonucleotide sequences used to generate a completed substrate reagent from a single substrate precursor in the presence of an excess of dNTP's and polymerase, using target as a template, as described in Example 7.

Target Dependent Synthesis of Substrate Reagent Using Substrate Precursor and Polymerase This example demonstrates yet another type of target-initiated synthesis of a completed substrate reagent, wherein the substrate reagent is formed from a single substrate precursor, containing a CAM, in the presence of an excess of dNTP's, polymerase, and a target sequence, as illustrated in FIG. 5. The target sequence in this example serves as template for hybridization and extension of the modified substrate precursor $_{Me}SP_3'$ in the presence of the dNTP's and a polymerase (Klenow), as shown in FIG. 21. Once synthesized, this substrate reagent-target duplex can be cut in the presence of Mlu I restriction endonuclease to produce an activated substrate reagent and an accumulation of oligonucleotide cleavage product, as demonstrated in Examples 8 and 9. The oligonucleotide sequences used in this example are shown in FIG. 21.

Similarly to the previous Example 6, the location of a methylphosphonate internucleotide linkage near the point of polymerase extension from the CAM-modified substrate precursor was seen as potentially interfering with the required action of the enzyme, in this case a polymerase. In order to evaluate the influence of the methylphosphonate CAM modification on polymerase extension, the corresponding wild type oligonucleotide $SP_3'$ was synthesized for use as a control in the comparison of extension efficiency with the modified substrate precursor.

Oligonucleotides $TIC_1$ and $^{32}P$-$TIC_1$ (7,000 Ci/mmole, used as a gel marker) were the same as in Example 6.

DNA polymerase I Large Fragment (Klenow), at a concentration of 5 units/µl, was purchased from New England Biolabs, Inc.

Deoxyadenosine 5'-triphosphate [alpha-$^{32}$p] ($\alpha^{32}$P-dATP) and deoxynucleoside-5'-triphosphates (dATP, dCTP, dGTP, and dTTP) were the same as used in Example 3. The dATP used in this example was adjusted to a specific activity of approximately 4,000 dpm/pmole by mixing the appropriate amount of $\alpha^{32}$P-dATP and dATP.

Oligonucleotide $SP_3'$ (Control Substrate Precursor 3') and methylphosphonate-containing oligonucleotide $_{Me}SP_3'$ (Substrate Precursor 3') were synthesized and purified, as described in Example 1.

A 10×reaction buffer was prepared as 500 mM Tris-HCl (pH 7.9), 100 mM $MgCl_2$, 1M NaCl, and 10 mM DTT.

All polymerase extension reactions were run in a final volume of 15 µl of 1×reaction buffer and contained each of the dNTP's at a concentration of 66.7 µM, as well as 1 unit of Klenow, and 2 pmoles of $TIC_1$ (unlabeled). The products resulting from polymerase extension were designed to be radioactive (from incorporation of radioactive dATP (4,000 dpm/pmole) during polymerase extension) to provide a means for subsequent visualization. The reactions also contained the following:

| Reaction | $SP_3'$ (pmoles) | $_{Me}SP_3'$ (pmoles) |
|---|---|---|
| 1 | 0.0 | 0.0 |
| 2 | 0.0 | 0.0 |
| 3 | 0.0 | 0.4 |
| 4 | 0.0 | 0.4 |
| 5 | 4.0 | 0.0 |
| 6 | 4.0 | 0.0 |

The reaction mixtures were heated to 90° C. for 2 minutes, and then cooled to room temperature to effect annealing of the primers to the target sequences. (Klenow polymerase, in a volume of 5 µl, was added to each reaction after this step, resulting in a final reaction volume of 15 µl) The extension reactions were allowed to proceed for 1 hour at 37° C. The reactions were stopped by adding 15 µl of dye reagent to each reaction, followed by heating to 90° C. for 2 minutes and then cooling to room temperature. The reaction products were analyzed by running the reactions on denaturing 15% PAGE, followed by visualization of the radioactive products using a PhosphorImager™ with ImageQuant™ software.

Figure 22:
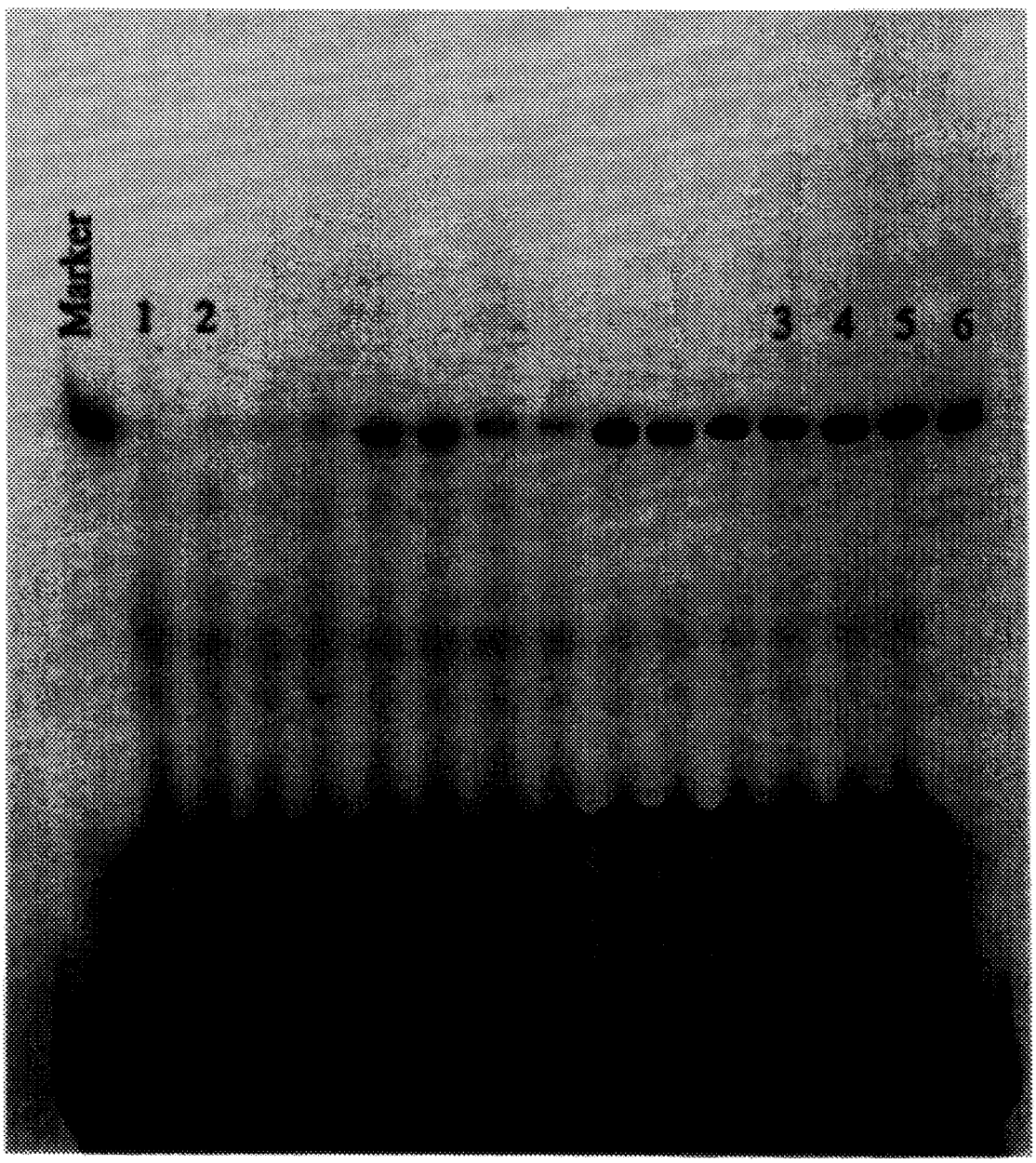
FIG. 22 is the PhosphorImager™ graphic printout of the polyacrylamide gel used to separate the products generated in Example 7.

A printout of the data from the PhosphorImager™ is shown in FIG. 22. Lanes 1–6 correspond to reactions 1–6, respectively. Radioactive $TIC_1$ (30-mer) was loaded on either side of the gel as a marker. As seen in Lanes 3, 4, 5, and 6, the expected 30-mer extension product was formed equally well with either the wild type control substrate precursor ($SP_3'$, Lanes 5 and 6) or the methylphosphonate-containing modified primer substrate precursor ($_{Me}SP_3'$, Lanes 3 and 4). Reactions in the absence of primer (Lanes 1 and 2) show no sign of 30-mer extension product, confirming that the products observed in Lanes 3–6 are indeed extension products from the respective substrate precursors.

EXAMPLE 8

Target-Dependent Synthesis of Oligonucleotides Using Klenow Polymerase

Figure 23:
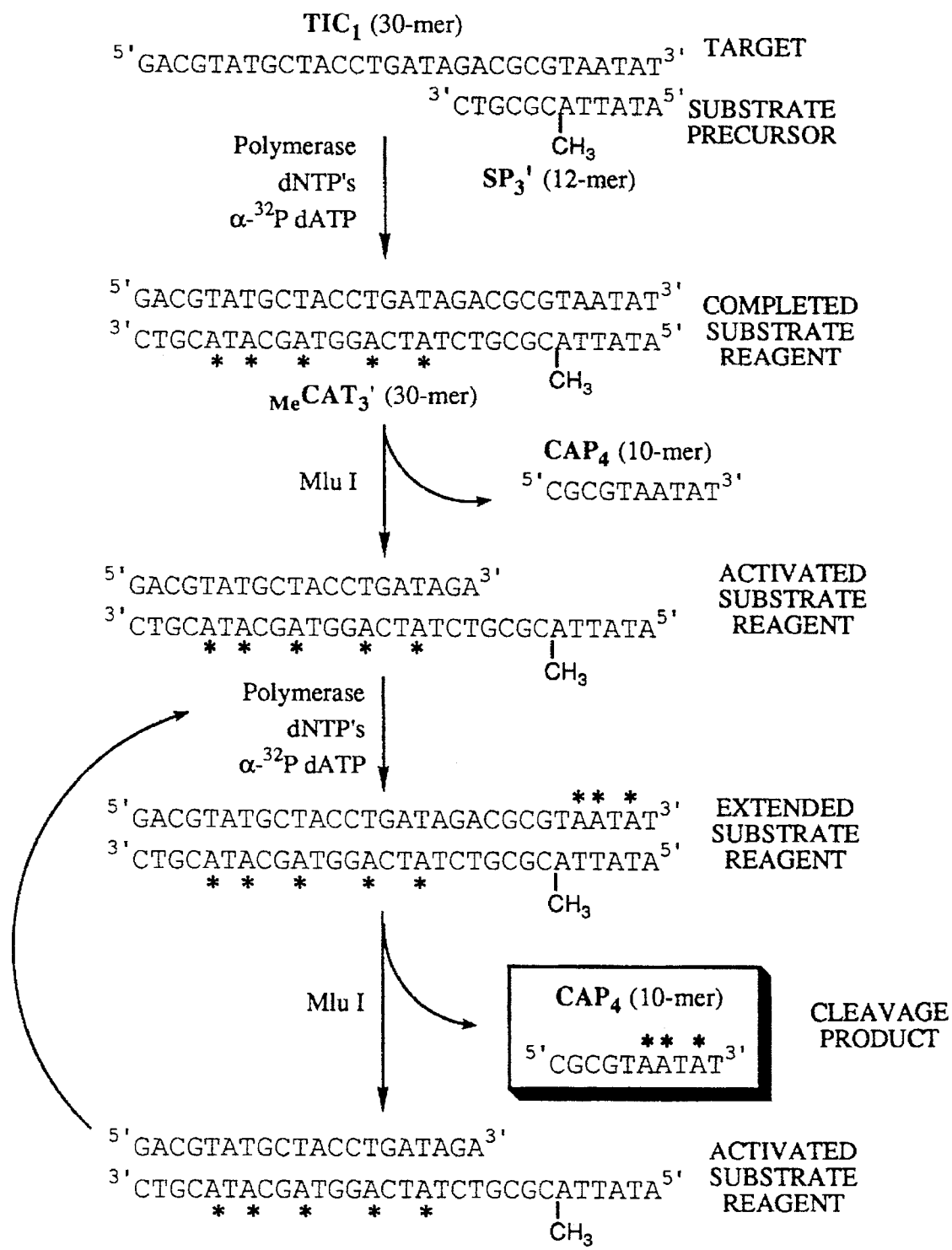
FIG. 23 illustrates the oligonucleotide sequences used to generate a cleavage product from a target-initiated substrate reagent, as described in Examples 8 and 9.

This example demonstrates the preparation of a completed substrate reagent (using a single substrate precursor), followed by oligonucleotide synthesis. The production of oligonucleotide products from the completed substrate reagent occurs as a result of the additional presence of a cutting agent (Mlu I) to simultaneously generate both the activated substrate reagent and cleavage product, as illustrated in FIG. 23. The target sequence $TIC_1$ serves as a template for substrate precursor ($_{Me}SP_3'$) which extends in the presence of Klenow polymerase and dNTP's to form the completed substrate reagent ($_{Me}CAT_3'$). Radioactive dATP was employed in this reaction as a means to visualize the completed substrate reagent and cleavage products after PAGE.

The resulting substrate reagent duplex is designed to be cleaved only on the upper strand, by cutting agent Mlu I, thus releasing oligonucleotide product ($CAP_4$, a 10-mer) and a target-activated substrate reagent, which can then be cycled to generate additional $CAP_4$ oligonucleotide product. The yield of product in this example can be estimated by comparison of the radioactive signal of the desired 10-mer CAP$_4$ oligonucleotide product (three radioactive phosphates) to that of the 30-mer substrate reagent (five radioactive phosphates).

It should be noted that, where the target sequence is flanked by additional nucleotides on its 5'- and 3'-ends (as is expected with a target obtained from a clinical sample), the resulting extension product will also contain complementary flanking sequence. Consequently, both the activated substrate reagent and the first oligonucleotide product released following the initial cutting step in this type of target initiation will be of an undefined length, as illustrated in FIG. 5. The undefined length of the activated substrate reagent will not affect its function in the synthesis of subsequent oligonucleotide cleavage products, which will then be of the desired defined length.

Oligonucleotide TIC$_1$ (target sequence), $^{32}$P-TIC$_1$ (7,000 Ci/mmole, used as a gel marker), $_{Me}$SP$_3$', Klenow polymerase, dNTP's, $\alpha^{32}$P-dATP, and 10×reaction buffer were the same as in Example 7.

Radioactive $\gamma^{32}$p-ATp and T$_4$ polynucleotide kinase were the same as in Example 6.

Oligonucleotide CAP$_4$ (10-mer), used as a gel marker was synthesized and purified, as described in Example 1.

The marker oligonucleotide CAP$_4$ was phosphorylated on its 5'-end to a specific activity of approximately 7,000 Ci/mmole using $\gamma^{32}$P-ATP and T$_4$ polynucleotide kinase. Excess ATP was separated from the labeled oligonucleotide by passing the reaction over a Sephadex® g 50/50 column.

MIU I restriction endonuclease, at a concentration of 10 units/µl, was purchased from New England Biolabs, Inc.

The dATP used in this example was adjusted to a specific activity of approximately 400 dpm/pmole by mixing the appropriate amount of the $\alpha^{32}$P-dATP and dATP.

All reactions were run in a final volume of 20 µl of 1×reaction buffer, and contained each dNTP at a concentration of 50 µM, 1 unit of Klenow, 10 units of Mlu I, and 10 pmoles of $_{Me}$SP$_3$'. The reaction mixtures also contained the following:

| Reaction | Target TIC$_1$ (pmoles) |
| --- | --- |
| 1 | 10.0 |
| 2 | 10.0 |
| 3 | 3.3 |
| 4 | 3.3 |
| 5 | 1.1 |
| 6 | 1.1 |
| 7 | 0.0 |
| 8 | 0.0 |

The reaction mixtures were heated to 90° C. for 2 minutes, and then cooled to room temperature to effect annealing of the primers to the target sequences. (Klenow polymerase and Mlu I restriction enzyme were added as a mixture to the reaction mixtures in a volume of 5 µl after this step, resulting in a final reaction volume of 20 µl) The reactions were set up in 1.5 ml screw top tubes containing an "o-ring" in the cap (available from Starstedt, Inc., Newton, N.C.) such that the reactions could be submerged in a constant temperature water bath to prevent evaporation. The synthesis reactions were allowed to run overnight (16 hours) at 40° C., and then stopped by adding 20 µl of dye reagent to each reaction mixture. This was followed by heating to 90° C. for 2 minutes, and then cooling to room temperature. The resulting reaction products were analyzed by running the reactions on denaturing 20% PAGE, followed by visualization of the radioactive products using a PhosphorImager™ with ImageQuant™ software.

Figure 24:
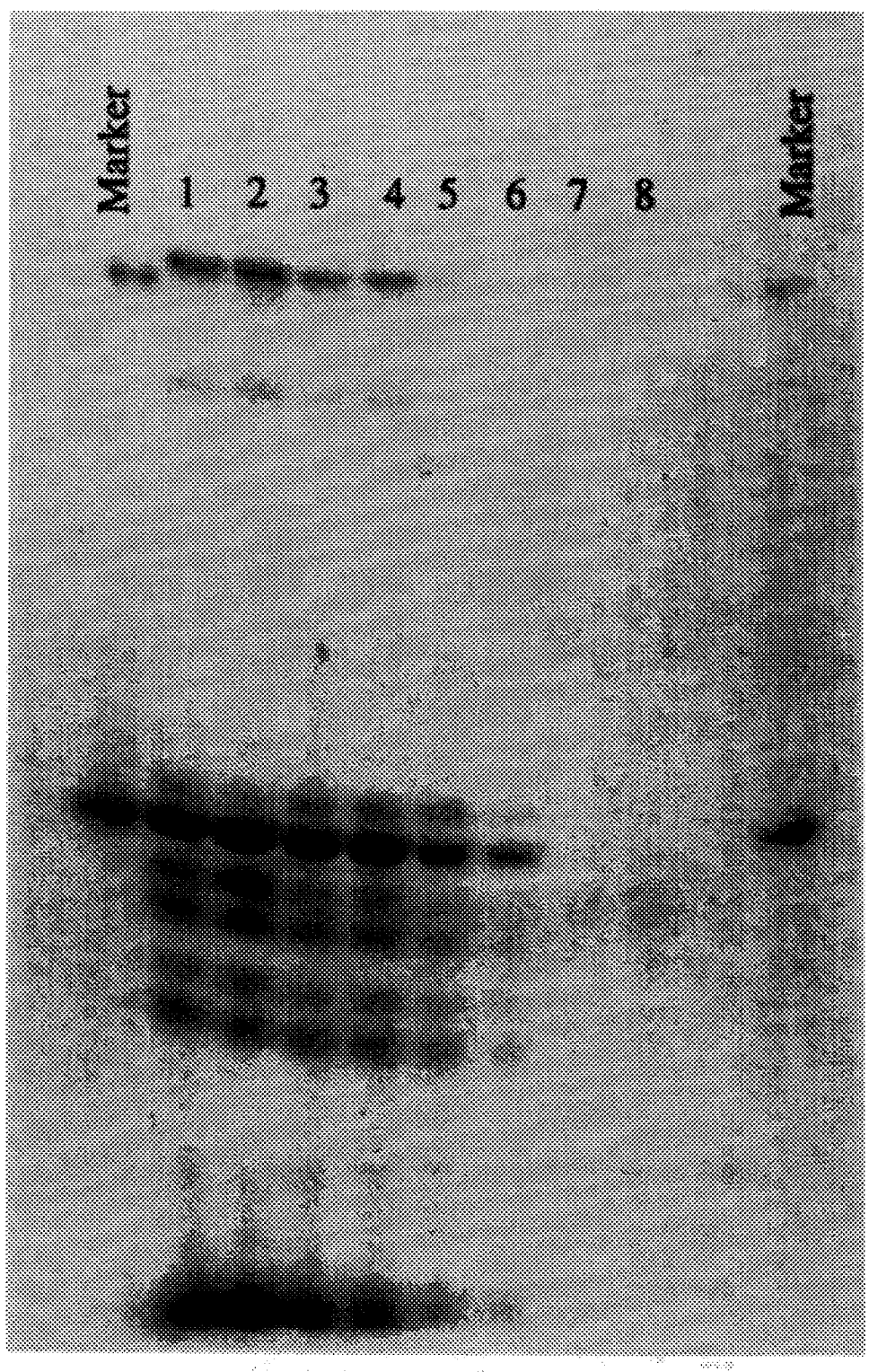
FIG. 24 is the PhosphorImager™ graphic printout of the polyacrylamide gel used to separate the products generated in Example 8.

A printout of the data from the PhosphorImager™ is shown in FIG. 24. Lanes 1–8 correspond to reactions 1–8, respectively. A mixture of $^{32}$P-labeled TIC$_1$ and $^{32}$P-labeled CAP$_4$ was loaded on either side of the gel to serve as markers (30-mer and 10-mer, respectively). The expected 30-mer substrate reagent and the corresponding 10-mer oligonucleotide product (CAP$_4$) were formed in all reactions containing target (TIC$_1$; e.g., Lanes 1–6). In contrast, neither product appeared in the "no target" control reactions (Lanes 7 and 8). The 30-mer substrate reagent generated in this reaction runs slightly slower than the 30-mer TIC$_1$ marker. This is to be expected, because the substrate reagent contains one fewer negative charge than the TIC$_1$ target, or marker, due to the presence of the single methylphosphonate modification initially present in the substrate precursor $_{Me}$SP$_3$'.) Additionally, the amount of product (CAP$_4$) produced in the reactions corresponds to the amount of starting sequence.

The number of oligonucleotides synthesized by each activated substrate reagent can be estimated by comparison of the intensity of the product signal (CAP$_4$, containing 3 radioactive phosphates) to that of the substrate reagent ($_{Me}$CAT$_3$', containing 5 radioactive phosphates) and normalizing the signals, with respect to the number of radioactive phosphates. Based on quantitation using the ImageQuant™ software, 20 to 50 oligonucleotides were synthesized for each target molecule in this example.

EXAMPLE 9

Target-Dependent Synthesis of Oligonucleotides Using Taq Polymerase

This example demonstrates the target-initiated synthesis of an oligonucleotide (as described in Example 8) using Taq polymerase instead of Klenow polymerase.

All of the reagents used in this example were the same as used in Example 8, with the exception of the following.

Taq polymerase was used instead of Klenow polymerase. AmpliTaq™ DNA polymerase was obtained from Perkin-Elmer/Cetus at a concentration of 5 units/µl.

The dATP in this example was adjusted to a specific activity of approximately 4,000 dpm/pmole by mixing the appropriate amounts of $\alpha^{32}$P-dATP and dATP.

All reactions were run in a final volume of 20 µl of 1×reaction buffer and contained each dNTP in a concentration of 50 µM, 2.5 units of AmpliTaq™ DNA polymerase, 10 units of Mlu I, and 2.0 pmoles of substrate precursor, $_{Me}$SP$_3$'. In addition, the reactions mixtures also contained the following:

| Reaction | Target TIC$_1$ (pmoles) |
| --- | --- |
| 1 | 1.0 |
| 2 | 1.0 |
| 3 | 0.33 |
| 4 | 0.33 |
| 5 | 0.11 |
| 6 | 0.11 |
| 7 | 0.0 |
| 8 | 0.0 |

The synthesis reactions were set up and allowed to run overnight (16 hours), as described in Example 8.

Figure 25:
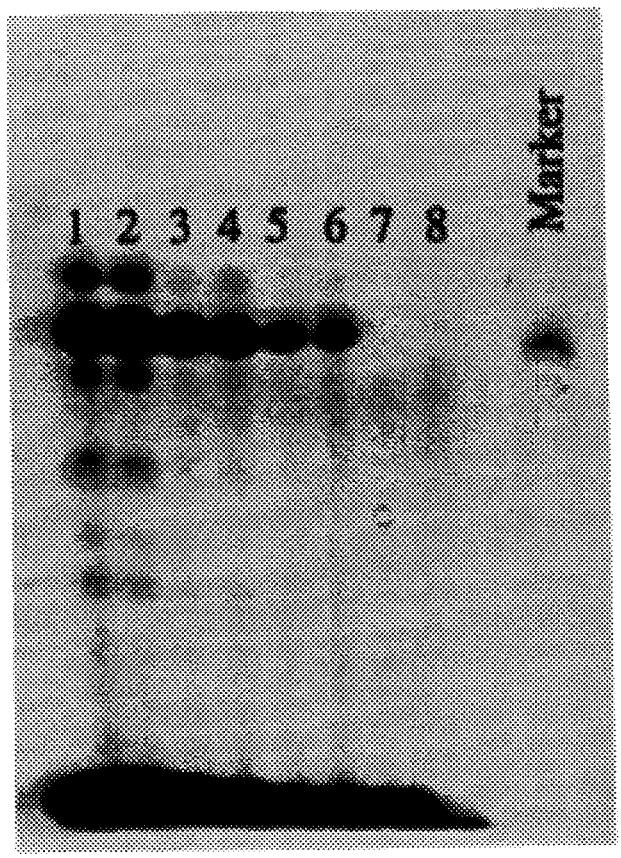
FIG. 25 is the PhosphorImager™ graphic printout of the polyacrylamide gel used to separate the products generated in Example 9.

A printout of the data from the PhosphorImager™ is shown in FIG. 25. Lanes 1–8 correspond to reactions 1–8, respectively. A mixture of $^{32}$P-labeled $TIC_1$ and $CAP_4$ was loaded on the right side of the gel to serve as markers (30-mer and 10-mer, respectively). As seen in Lanes 1–6, the expected 30-mer substrate reagent (slightly slower moving than the 30-mer marker, as previously explained in Example 8) is formed in all reactions containing target sequence ($TIC_1$). Additionally, a very strong signal can be seen in the area of the 10-mer $CAP_4$ marker. In contrast, no signals were produced from the "no target" control reactions, Lanes 7 and 8. The visible amount of 11-mer product, also produced in the oligonucleotide synthesis reactions (e.g., Lanes 1 an 2), is probably due to the fact that Taq polymerase is known to add one or more nucleotides onto the 3'-ends of extension products beyond the end of the template. Based on quantitation derived from ImageQuant™ software, 160 to 240 oligonucleotide products were synthesized for every target molecule present in these reactions.

What is claimed is:

1. A method for generating a cascade of oligonucleotide products comprising:
    (a) contacting a first nucleic acid template sequence having a cutting attenuation modification with a primer complementary to a portion of said template sequence, an excess of nucleoside triphosphates, and an agent for polymerization to generate a first nucleic acid sequence complementary to said first template sequence, thus forming a first duplex nucleic acid sequence;
    (b) contacting said first duplex nucleic acid sequence with a first nucleases to generate a first oligonucleotide cleavage product while the primed first template sequence remains substantially intact due to the presence of the cutting attenuation modification;
    (c) contacting a second nucleic acid template sequence having a cutting attenuation modification with said first oliganucleotide cleavage product, an excess of nucleoside triphosphates, and an agent for polymerization to a generate a second nucleic acid sequence complementary to said second template sequence, thus forming a second dulplex nucleic acid sequence, wherein said first oligonucleotide cleavage product acts as a primer for said second nucleic acid template sequence;
    (d) contacting said second duplex nucleic acid sequence with a second nuclease to generate a second oligonucleotide cleavage product while the primed second template sequence remains substantially intact due to the presence of the cutting attenuation modification; and
    (e) repeating steps (b) through (d) thereby generating a cascade of oligonucleotide products.

2. The method of claim 1 wherein said primer is hybridized to said template sequence prior to addition of the other reagents in step (a).

3. The method of claim 2 wherein said primer is attached to said template sequence through a linker arm.

4. The method of claim 4 wherein said cutting attenuation modification of said first template sequence and/or said second template sequence is a chemical modification to the template sequence backbone and the first and/or second nuclease is a restriction enzyme.

5. The method of claim 4 wherein said cutting attenuation modification is a methylphosphonate modification.

6. The method of claim 1 wherein the formation of said first template sequence is catalyzed by the presence of target nucleic acid sequence.

7. The method of claim 6 wherein said target nucleic acid sequence acts as a template for the formation of said first template sequence.

8. The method of claim 4 wherein said target nucleic acid sequence acts as a ligation template for the formation of said first template sequence from two or more contiguously hybridizing template precursors.

9. The method of claim 7 wherein said target nucleic acid sequence acts as a polymerization template for the formation of said first template sequence.

10. The method of claim 1 wherein the 3'-end of said second template sequence extends beyond the 5'-end of said first oligonucleotide cleavage product when said cleavage product hybridizes to said second template sequence in order to prime in situ synthesis of said second complementary oligonucleotide sequence.

11. The method of claim 1 wherein the 5'-end of said first oligonucleotide cleavage product extends beyond the 3'-end of said second template sequence when said cleavage product hybridizes to said second template sequence in order to prime in situ synthesis of said second complementary oligonucleotide sequence.

12. The method of claim 1 wherein the 3'-end of said second template sequence extends beyond the 5'-end of first oligonucleotide cleavage product and said first cleavage product extends beyond the 3'-end of said second template sequence when said cleavage product hybridizes to said second template sequence in order to prime in situ synthesis of said second complementary oligonucleotide sequence.

13. The method of claim 2 wherein the formation of said first template sequence is catalyzed by the presence of target nucleic acid sequence.

14. The method of claim 4 wherein said cutting attenuation modification is a methylthiophosphonate modification.

15. The method of claim 1 wherein said first nuclease and said second nuclease are the same.

16. The method of claim 1 wherein at least one of said first template sequence and said second template sequence has a first region complementary to said oligonucleotide cleavage product and a second region complementary to said primer, wherein said first and second regions fire separated by a third intervening region.

17. A method for generating a cascade of oligonucleotide products comprising:
    (a) contacting a first nucleic acid template sequence having a first region complementary to a first oligonucleotide cleavage product, a second region complementary to a first primer, a third intervening region separating said first and second regions, and a cutting attenuation modification with said first primer, an excess of nucleoside triphosphates, and an agent for polymerization to generate a first duplex nucleic acid sequence;
    (b) contacting said first duplex nucleic acid sequence with a first nuclease to release a first oligonucleotide cleavage product while the primed first template sequence remains substantially intact due to the presence of the cutting attenuation modification;
    (c) contacting a second nucleic acid template sequence having a first region complementary to a second oligonucleotide cleavage product, a second region complementary to a second primer, a third intervening region separating said first and second regions, and a cutting attenuation modification with said first oligonucleotide cleavage product, an excess of nucleoside triphosphates, and an agent for polymerization to generate a second duplex nucleic acid sequence;
    (d) contacting said second duplex nucleic acid sequence with a second nuclease to release a second oligonucleotide cleavage product while the primed second template sequence remains substantially intact due to the presence of the cutting attenuation modification;

(e) contacting said first primed template sequence and/or said second primed template sequence with an excess of nucleoside triphosphates and an agent for polymerization to form said first duplex nucleic acid sequence and/or said second duplex nucleic acid sequence; and (f) repeating steps (b) through (e), wherein said first oligonucleotide cleavage product acts as said second primer for said second nucleic acid template sequence, thereby generating a cascade of Oliaonucleotide products.

18. The method of claim 17 wherein said first primer is hybridized to said template sequence prior to addition of the other reagents in step (a).

19. The method of claim 18 wherein said first primer is attached to said template sequence through a linker arm.

20. The method of claim 18 wherein the formation of said first template sequence is catalyzed by the presence of target nucleic acid sequence.

21. The method of claim 17 wherein said cutting attenuation modification of said first template sequence and/or said second template sequence is a chemical modification to the template sequence backbone and the first and/or second nuclease is a restriction enzyme.

22. The method of claim 21 wherein said cutting attenuation modification is a methylphosphonate modification.

23. The method of claim 21 wherein said cutting attenuation modification is a methylthiophosphonate modification.

24. The method of claim 17 wherein the formation of said first template sequence is catalyzed by the presence of target nucleic acid sequence.

25. The method of claim 24 wherein said target nucleic acid sequence acts as a template for the formation of said first template sequence.

26. The method of claim 25 wherein said target nucleic acid sequence acts as a ligation template for the formation of said first template sequence from two or more contiguously hybridizing template sequence precursors at least one of said substrate precursors containing a cutting.

27. The method of claim 25 wherein said target nucleic acid sequence acts as a polymerization template for the formation of said first template sequence.

28. The method of claim 17 wherein the 3'-end of said second template sequence extends beyond the 5'-end of said first oligonucleotide cleavage product when said cleavage product hybridizes to said second template sequence in order to prime in situ synthesis of said second duplex nucleic acid sequence.

29. The method of claim 28 wherein the 5'-end of said first oligonucleotide cleavage product extends beyond the 3'-end of said second template sequence when said cleavage product hybridizes to said second template sequence in order to prime in situ synthesis of said second duplex nucleic acid sequence.

30. The method of claim 17 wherein the 3'-end of said second template sequence extends beyond the 5'-end of said first oligonucleotide cleavage product and the 5'-end of said first oligonucleotide cleavage product extends beyond the 3+-end of said second template sequence when said cleavage product hybridizes to said second template sequence in order to prime in situ synthesis of said second duplex nucleic acid sequence.

31. The method of claim 17 wherein said first nuclease and said second nuclease are the same.

32. The method of claim 31 wherein said cutting attenuation modification of said first template sequence and said second template sequence is a chemical modification to the template sequence backbone and said first and second nucleases are the same restriction enzyme.

33. The method of claim 32 wherein said cutting attenuation modification is a methylphosphonate modification.

34. The method of claim 32 wherein said cutting attenuation modification is a methylthiophosphonate modification.

35. A method for generating a cascade of oligonucleotide products comprising;

(a) contacting a series of nucleic acid template sequences each having a first region complementary to a desired oligonucleotide cleavage product, a second region complementary to a primer and a cutting attenuation modification with said primer, an excess of nucleoside triphosphates, and an agent for polymerization to generate duplex nucleic acid sequences;

(b) contacting said extended duplex nucleic acid sequences with nucleases to release an oligonucleotide cleavage product and a primed template sequence from each duplex nucleic acid sequence; and (c) repeating steps (a) and (b), wherein the primer for each template sequence other than the first template sequence in said series of template sequences is the cleavage product from the previous duplex nucleic acid sequence formed in said series of template sequences, thereby generating a cascade of oligonucleotide products.

36. The method of claim 35 wherein the formation of said first template sequence is catalyzed by the presence of target nucleic acid sequence.

37. The method of claim 35 wherein the 3'-end of each template sequence other than the first template sequence in said series of template sequences extends beyond the 5'-end of the previous oligonucleotide cleavage product when said oligonucleotide cleavage product hybridizes to said template sequence in order to prime in situ synthesis of a complementary oligonucleotide sequence.

38. The method of claim 35 wherein the 5'-end of each of oligonucleotide cleavage products extends beyond the 3'-end of the next template sequence in said series of template sequences when said cleavage product hybridizes to said next template sequence in order to prime in situ synthesis of a complementary oligonucleotide sequence.

39. The method of claim 35 wherein the 3'-end of each template sequence other than the first template sequence in said series of template sequences extends beyond the 5'-end of the previous oligonucleotide cleavage product and the 5'-end of each of said oligonucleotide cleavage products extends beyond the 3'-end of the next template sequence in said series of template sequences when said cleavage product hybridizes to said next template sequence in order to prime in situ synthesis or a complementary oligonucleotide sequence.

40. The method of claim 35 wherein at least one of said template sequences in said series of template sequences has a first region complementary to said oligonucleotide cleavage product and a second region complementary to said primer, wherein said first and second regions are separated by a third intervening region.

41. The method of claim 40 wherein each of said template sequences in said series of template sequences has a first region complementary to said oligonucleotide cleavage product and a second region complementary to said primer, wherein said first and second regions are separated by a third intervening region.

42. The method of claim 36 wherein said nucleases are the same.

43. The method of claim 41 wherein each of said cutting attenuation modifications is a chemical modification to the template sequence backbone and said nucleases are the same restriction enzyme.

44. The method of claim 35 wherein the 3'-end of each template sequence other than the first template sequence in said series of template sequences extends beyond the 5' end of the previous oligonucleotide cleavage product and the 5'-end of each of said oligonucleotide cleavage products extends beyond the 3'-end of the next template sequence in said series of template sequences when said cleavage product hybridizes to said next template sequence, each of said template sequences in said series of template sequences has a first region complementary to said oligonucleotide cleavage product and a second region complementary to said primer, wherein said first and second regions are separated by a third intervening region, and each of said nucleases are the same.

* * * * *

UNITED STATES PATENT AND TRADEMARK OFFICE
CERTIFICATE OF CORRECTION

PATENT NO. : 5,645,987
DATED : July 8, 1997
INVENTOR(S) : Richards

It is certified that error appears in the above-identified patent and that said Letters Patent is hereby corrected as shown below:

Column 3, line 12, delete the second "than".

Column 4, line 51, replace "FIG. 12A and 12" with --FIG. 12A and 12B--.

Column 13, line 48, delete "and".

Column 18, line 57, replace "Just" with --just--.

Column 24, line 19, add --.-- after "environment".

Column 24, line 44, replace "Oliaonucleotide" with --Oligonucleotide--.

Column 27, line 22, replace "$^{SMe}CAT_1$'" with --$_{SMe}CAT_1$'--.

Column 29, Line 61, delete "5".

Column 31, line 33, replace "Junction" with --junction--.

Column 32, line 63, replace "qunatitative" with --quantitative--.

Column 34, line 23, replace "15 μl)" with --15 μl.)--.

Column 35, line 21, replace "$\gamma^{32}$p-ATp" with --$\gamma^{32}$P-ATP--.

Column 37, Line 30, replace "nucleases" with --nuclease--.

UNITED STATES PATENT AND TRADEMARK OFFICE
CERTIFICATE OF CORRECTION

PATENT NO. : 5,645,987
DATED : July 8, 1997
INVENTOR(S) : Richards

It is certified that error appears in the above-identified patent and that said Letters Patent is hereby corrected as shown below:

Column 37, line 36, replace "oliganucleotide" with --oligonucleotide--.

Column 37, line 38, delete the first "a".

Column 37, line 48, add --,-- after "(d)".

Column 37, line 55, replace the second "claim 4" with --claim 1--.

Column 38, line 1, replace "claim 4" with --claim 7--.

Column 38, line 38, replace "fire" with --are--.

Column 39, line 11, replace "Oliaonucleotide" with --oligonucleotide--.

Column 39, line 39, delete "at least one of said substrate precursors containing a cutting".

Column 39, line 60, replace "3+-end" with --3'-end--.

Column 40, line 52, replace "or" with --of--

Signed and Sealed this

Twenty-third Day of June, 1998

Attest:

BRUCE LEHMAN

Attesting Officer

Commissioner of Patents and Trademarks